United States Patent
Sprogøe et al.

(10) Patent No.: US 8,758,780 B2
(45) Date of Patent: Jun. 24, 2014

(54) SUBCUTANEOUS PALIPERIDONE COMPOSITION

(75) Inventors: Kennett Sprogøe, Palo Alto, CA (US); Ulrich Hersel, Heidelberg (DE); Harald Rau, Dossenheim (DE); Guillaume Maitro, Mannheim (DE); Thomas Wegge, Heidelberg (DE)

(73) Assignee: Ascendis Pharma AS, Hellerup (DK)

( * ) Notice: Subject to any disclaimer, the term of this patent is extended or adjusted under 35 U.S.C. 154(b) by 0 days.

(21) Appl. No.: 13/500,623

(22) PCT Filed: Oct. 6, 2010

(86) PCT No.: PCT/EP2010/064880
§ 371 (c)(1),
(2), (4) Date: May 8, 2012

(87) PCT Pub. No.: WO2011/042453
PCT Pub. Date: Apr. 14, 2011

(65) Prior Publication Data
US 2012/0277253 A1    Nov. 1, 2012

(30) Foreign Application Priority Data

Oct. 6, 2009  (EP) .................................... 09172336
Dec. 23, 2009 (EP) .................................... 09180552
Jul. 30, 2010 (EP) .................................... 10171512

(51) Int. Cl.
*A61K 9/00*    (2006.01)

(52) U.S. Cl.
USPC ........................................................ 424/400

(58) Field of Classification Search
None
See application file for complete search history.

(56) References Cited

U.S. PATENT DOCUMENTS

| 5,254,556 | A | 10/1993 | Janssen et al. |
| 5,965,168 | A | 10/1999 | Mesens et al. |
| 7,879,588 | B2 | 2/2011 | Vetter et al. |
| 7,968,085 | B2 | 6/2011 | Hersel et al. |
| 2007/0197591 | A1 | 8/2007 | Boom et al. |
| 2007/0197592 | A1* | 8/2007 | Boom et al. .................. 514/317 |
| 2008/0241102 | A1 | 10/2008 | Hersel et al. |
| 2009/0163519 | A1* | 6/2009 | Vermeulen et al. ...... 514/259.41 |
| 2010/0291021 | A1 | 11/2010 | Vetter et al. |

(Continued)

FOREIGN PATENT DOCUMENTS

| EP | 1625856 | 2/2006 |
| WO | WO 99/25354 | 5/1999 |

(Continued)

OTHER PUBLICATIONS

"Schizophrenia" by Mayo Clinic Staff obtained from http://www.mayoclinic.com/health/schizophrenia/DS00196 on Mar. 21, 2012.*
Bishara et al., "Upcoming Agents for the Treatment of Schizophrenia", Drugs, 2008, pp. 2269-2292, vol. 68, No. 16, Adis Data Information B.V.
DSMIV-TR. Diagnostic and Statistical Manual of Mental Disorders, Revised 4$^{th}$ Edition, 1994, American Psychiatric Association.

(Continued)

*Primary Examiner* — Carlos Azpuru
*Assistant Examiner* — Casey Hagopian
(74) *Attorney, Agent, or Firm* — Frommer Lawrence & Haug LLP

(57) ABSTRACT

The present invention relates to pharmaceutical composition for subcutaneous injection comprising a paliperidone compound wherein the composition releases the paliperidone with an immediate onset of action and continuously for at least 3 weeks, and wherein the composition has a pharmacokinetic profile in vivo with substantially no burst release of the paliperidone. The compositions are useful as medicaments for the treatment of psychotic disorders and diseases.

14 Claims, 7 Drawing Sheets

(56) References Cited

U.S. PATENT DOCUMENTS

| | | |
|---|---|---|
| 2011/0009315 A1 | 1/2011 | Hersel et al. |
| 2011/0053848 A1 | 3/2011 | Cleemann et al. |
| 2011/0112021 A1 | 5/2011 | Rau et al. |
| 2012/0058084 A1 | 3/2012 | Rau et al. |

FOREIGN PATENT DOCUMENTS

| | | |
|---|---|---|
| WO | WO 2006/003014 | 1/2006 |
| WO | WO 2006/017537 | 2/2006 |
| WO | WO 2008/128436 | 10/2008 |
| WO | WO 2008/153611 | 12/2008 |
| WO | WO 2009/015828 | 2/2009 |

OTHER PUBLICATIONS

English et al., "Orally Effective Acid Prodrugs of the β-Lactamase Inhibitor Sulbactam", J. Med. Chem., 1990, pp. 344-347, vol. 33, American Chemical Society, U.S.

Hough et al., "Safety and tolerability of deltoid and gluteal injections of paliperidone palmitate in schizophrenia", Progress in Neuro-Psychopharmacology & Biological Psychiatry, Aug. 2009, pp. 1022-1031, vol. 33, Elsevier, Inc.

Jenkem Technology USA Product List, Apr. 2009.

Ould-Ouali et al., "Self-Assembling PEG-$p$(CL-co-TMC) copolymers for oral delivery of poorly water-soluable drugs: a case study with risperdone", J. of Controlled Release, 2005, pp. 657-668, vol. 102, Elsevier.

* cited by examiner

SUBCUTANEOUS PALIPERIDONE COMPOSITION

The present application claims priority from PCT Patent Application No. PCT/EP2010/064880 filed on Oct. 6, 2010, which claims priority from European Patent Application Nos. EP 09172336.1 filed on Oct. 6, 2009, EP 09180552.3 filed on Dec. 23, 2009, and EP 10171512.6 filed on Jul. 30, 2010, the disclosures of which are incorporated herein by reference in their entirety.

BACKGROUND OF THE INVENTION

1. Field of the Invention

The present invention relates to a pharmaceutical composition for subcutaneous injection comprising a paliperidone compound. In particular the composition releases the paliperidone with an immediate onset of action and has an extended release time. Moreover, the present invention relates to a pharmaceutical composition for subcutaneous injection comprising a paliperidone compound in a certain concentration. The present invention also relates to use of the compositions as well as methods of treatment and a kit of parts.

2. Background

It is noted that citation or identification of any document in this application is not an admission that such document is available as prior art to the present invention.

Paliperidone is an atypical antipsychotic indicated for the acute and maintenance treatment of schizophrenia. The drug exhibits significantly reduced side-effects compared to other anti-psychotic drugs used to treat both schizophrenia as well as bipolar disorder.

Chemically, paliperidone is 9-hydroxyrisperidone. Paliperidone and risperidone act via similar, if not identical, pathways; therapeutic effect may be due to a combination of D2 and 5-HT2A receptor antagonism. Paliperidone also has antagonist effect at $\alpha 1$ and $\alpha 2$ adrenergic receptors and at H1 histamine receptors. Other indications may involve bipolar mania and schizoaffective disorder, and like risperidone, its possible use in autism and Asperger's syndrome and Tourette's disorder may be of benefit to the patients. Risperidone was initially marketed as Risperdal and recently became generic.

Paliperidone recently received marketing approval as the first oral atypical antipsychotic with an extended release, which is achieved by an osmotic-controlled release oral delivery system. Paliperidone ER (WO-A 2006/017537) is marketed as Invega Sustenna. Unsaturated derivatives thereof are described in WO-A 2008/128436.

Other extended release oral dosage forms for paliperidone are under development. Due the presence of a secondary hydroxyl group, paliperidone may be provided as a prodrug. WO-A 2009/015828 details acid-labile low molecular weight prodrugs of paliperidone intended to undergo hydrolysis in the stomach.

It is of interest to develop very long-acting, injectable depots of paliperidone. There is great need to improve the compliance factor particularly in the treatment of schizophrenia. The development of once-weekly or even longer acting injectable depot formulations of paliperidone will mark a significant step forward to ensure continuous and steady supply of the effective medication.

In U.S. Pat. No. 5,965,168 is described compounds of formula I which are formulated in sustained release microparticles. Risperidone is mentioned as the preferred compound and risperidone is used as basis for all experimentals therein. FIG. 5 therein shows the plasma concentration time curves for the active moiety (sum of risperidone and paliperidone) after intramuscular injection of risperidone depot.

WO-A 2008/153611 describes sustained release formulations of risperidone and metabolites. Here, risperidone is mixed with a soluble thermoplastic polymer, forming an encapsulating residue upon injection from which risperidone is slowly released.

U.S. Pat. No. 5,254,556 reveals ester-linked prodrugs of paliperidone. The substance paliperidone palmitate is approved as a once monthly atypical antipsychotic intramuscular injection for treating schizophrenia and preventing recurrence of its symptoms. Paliperidone palmitate is formulated in a submicrocrystalline form.

Paliperidone palmitate due to its dissolution rate-limited absorption exhibits flip-flop kinetics, where the apparent half-life is controlled by the absorption rate constant. Additionally the volume of injected drug product also impacts the apparent rate constant. It was also discovered that deltoid injections result in a faster rise in initial plasma concentration, facilitating a rapid attainment of potential therapeutic concentrations. Consequently, to facilitate patients' attaining a rapid therapeutic concentration of paliperidone it is preferred to provide the initial loading dose of paliperidone palmitate in the deltoids. The loading dose should be from about 100 mg-eq. to about 150 mg-eq. of paliperidone provided in the form of paliperidone palmitate. After the first or more preferably after the second loading dose injection patients will be approaching a steady state concentration of paliperidone in their plasma and may be injected in either the deltoid or the gluteal muscle thereafter. However, it is preferred that the patients receive further injections in the gluteal muscle. US-A2009/0163519 outlines corresponding dosing regimen for long-acting injectable paliperidone esters of the palmitate type.

Other antipsychotic depot medications are also characterized by the need for concomitant oral medication or booster injections in order to obtain desired plasma levels of the active drug. For example, Risperdal Consta requires oral antipsychotic treatment during the initiation phase.

A preferred profile of a depot antipsychotic would be dosing once a month or even less frequent, without the need for additional oral or injectable medication. It would therefore be a significant step forward if a sustained release atypical antipsychotic formulation could also be characterized by having a fast onset. It is therefore an object of the current formulation to provide a long acting formulation in which the therapeutic plasma concentration is attained within the first 24 hours after dosing.

Though the gluteal muscle is the preferred site for paliperidone palmitate administration, there is a perception in the psychiatric community that injection in the gluteal muscle is psychologically distressing to the patients as well as intramuscular injection in general being associated with significant physical discomfort.

It would therefore be of benefit for the patient as well as the health care professional that the long acting depot could be administered by subcutaneous injection, which is perceived less painful and less invasive.

Paliperidone esters are not the only antipsychotic compounds being associated with complications following intramuscular injection. A novel long acting version of olanzapine, Zypadhera, is associated with a serious phenomenone of rapid absorption of the depot drug occurring in approximately 1 out of every 1000 injections. The phenomenone, post-injection delirium/sedation syndrome, is thought to relate to faster dissolution of the depot if a blood vessel is damaged or the drug is administered to a capillary bed during administration and thereby increasing blood flow near the depot and hence also increase the dissolution rate. This phenomenon potentially can occur with depots where the release profile of the drug is controlled in large part by surrounding blood flow. It is well described that this phenomenone is known risk of intramuscular injections (drugs. 2008; 68(16), 2269-92).

Therefore, it would be beneficial to have a long acting atypical antipsychotic formulation that can be administered by subcutaneous injection and that does not display large variation in absorption between injection sites. This would allow the health care professional to choose between preferred injection sites without increasing the variation of the plasma concentration of active drug as well as causing the patient minimal discomfort. Subcutaneous injection would also be perceived as significantly less invasive by patient and physician.

In addition, a formulation without the risk of post-injection delirium/sedation syndrome would greatly increase safety for the patients and reduce health care costs as the need for post injection patient monitoring is reduced.

An additional positive feature of administering subcutaneous injections is a reduced need for different needles dimensions for patients with differing body mass index (BMI). For example, according to the prescribing information for Invega® Sustenna™, different needle sizes are required for ensuring delivery of the depot to the muscular tissue in patients with varying amounts of subcutaneous fat.

Furthermore, studies of the long-acting injectable formulation of risperidone, which is dosed every two weeks, have indicated that D2-receptor occupancy remains relatively stable throughout the dosing interval, and this has been associated with low rates of rehospitalization in patients with schizophrenia, as well as a reduced risk of extrapyrimidal symptoms (EPS). It may, therefore, be desirable to achieve a stable plasma profile and, consequently, consistent D2-receptor occupancy throughout the day. Long acting atypical antipsychotic depots, therefore, offer advantages over oral dosing regimens, the latter being characterized by having larger variations in peaks and troughs in plasma concentrations. Long acting atypical antipsychotic depots therefore can reduce the incidence of EPS and/or sub-optimal efficacy. For this reason it is beneficial to have a small ratio between peak and trough plasma concentration, preferably less than 3 at steady state.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

Some relevant definitions for understanding the present invention are explained herein below.

"Psychotic disease or disorder" refers to those provided in the Diagnostic and Statistical Manual (DSM IV), American Psychological Association (APA). Those of ordinary skill in the art will appreciate that formulations of paliperidone compounds can be administered to psychiatric patients for all the known uses of risperidone. These mental disorders include, but are not limited to, schizophrenia; bipolar disorder or other disease states in which psychosis, aggressive behavior, anxiety or depression is evidenced. Schizophrenia refers to conditions characterized as schizophrenia, schizoaffective disorder and schizophreniform disorders, in DSM-IV-TR such as category 295.xx. Bipolar Disorder refers to a condition characterized as a Bipolar Disorder, in DSM-IV-TR such as category 296.xx including Bipolar I and Bipolar Disorder II. The DSM-IV-TR was prepared by the Task Force on Nomenclature and Statistics of the American Psychiatric Association, and provides clear descriptions of diagnostic categories. Pathologic psychological conditions, which are psychoses or may be associated with psychotic features include, but are not limited to the following disorders that have been characterized in the DSMIV-TR. Diagnostic and Statistical Manual of Mental Disorders, Revised, 3rd Ed. (1994). The numbers in parenthesis refer to the DSM-IV-TR categories. The skilled artisan will recognize that there are alternative nomenclatures, nosologies, and classification systems for pathologic psychological conditions and that these systems evolve with medical scientific progress. Examples of pathologic psychological conditions which may be treated include, but are not limited to, Mild Mental Retardation (317), Moderate Mental Retardation (318.0), Severe Mental Retardation (318.1), Profound Mental Retardation (318.2), Mental Retardation Severity Unspecified (319), Autistic Disorders (299.00), Rett's Disorder (299.80), Childhood Disintegrative Disorders (299.10), Asperger's Disorder (299.80), Pervasive Developmental Disorder Not Otherwise Specified (299.80), Attention Deficit/Hyperactivity Disorder Combined Type (314.01), Attention/Deficit Hyperactivity Disorder Predominately Inattentive Type (314.00), Attention-Deficit/Hyperactivity Disorder Predominately Hyperactive-Impulsive Type (314.01), Attention-Deficit/Hyperactivity Disorder NOS (314.9), Conduct Disorder (Childhood Onset and Adolescent Type 312.8), Oppositional Defiant Disorder (313.81), Disruptive Behavior Disorder Not Otherwise Specified (312.9), Solitary Aggressive Type (312.00), Conduct Disorder, Undifferentiated Type (312.90), Tourette's Disorder 15 (307.23), Chronic Motor Or Vocal Tic Disorder (307.22), Transient Tic Disorder (307.21), Tic Disorder NOS (307.20), Alcohol Intoxication Delirium (291.0), Alcohol Withdrawal Delirium (291.0), Alcohol-Induced Persisting Dementia (291.2), Alcohol Induced Psychotic Disorder with Delusions (291.5), Alcohol-Induced Psychotic Disorder with Hallucinations (291.3), Amphetamine or Similarly Acting Sympathomimetic Intoxication (292.89), Amphetamine or Similarly Acting Sympathomimetic Delirium (292.81), Amphetamine or Similarly Acting Sympathomimetic Induced Psychotic with Delusions (292.11), Amphetamine or Similarly Acting Sympathomimetic Induced Psychotic with Hallucinations (292.12), Cannabis-Induced Psychotic Disorder with Delusions (292.11), Cannabis-Induced Psychotic Disorder with Hallucinations (292.12), Cocaine Intoxication (292.89), Cocaine Intoxication Delirium (292.81), Cocaine-Induced Psychotic Disorder with Delusions (292.11), Cocaine-Induced Psychotic Disorder with Hallucinations (292.12), Hallucinogen Intoxication (292.89), Hallucinogen Intoxication Delirium (292.81), Hallucinogen-Induced Psychotic disorder with Delusions (292.11), Hallucinogen-Induced Psychotic disorder with Delusions (292.12), Hallucinogen-Induced Mood Disorder (292.84), Hallucinogen:-Induced Anxiety Disorder (292.89), Hallucinogen Related Disorder Not Otherwise Specified (292.9), Inhalant Intoxication (292.89), Inhalant Intoxication Delirium (292.81), Inhalant-Induced Persisting Dementia (292.82), Inhalant-Induced Psychotic Disorder with Delusions (292.11), Inhalant Induced Psychotic with Hallucinations (292.12), Inhalant-Induced Mood Disorder (292.89), Inhalant-Induced Anxiety Disorder (292.89), Inhalant-Related Disorder Not Otherwise Specified (292.9), Opioid Intoxication Delirium (292.81), Opioid Induced Psychotic Disorder with Delusions (292.11), Opioid Intoxication Delirium (292.81), Opioid-Induced Psychotic Disorder with Hallucinations (292.12), Opioid-Induced Mood Disorder (292.84), Phencyclidine (PCP) or Similarly Acting Arylcyclohexylamine Intoxication (292.89), Phencyclidine (PCP) or Similarly Acting Arylcyclohexylamine Intoxication Delirium (292.81), Phencyclidine (PCP) or Similarly Acting Arylcyclohexylamine Induced Psychotic Disorder with Delusions (292.11), Phencyclidine (PCP) or Similarly Acting Arylcyclohexylamine Induced Psychotic Disorder with Hallucinations (292.12), Phencyclidine (PCP) or Similarly Acting Arylcyclohexylamine Mood Disorder (292.84), Phencyclidine (PCP) or Similarly Acting Arylcyclohexylamine Induced Anxiety Disorder (292.89), Phencyclidine (PCP) or Similarly Acting Arylcyclohexylamine Related Disorder Not Otherwise Specified (292.9), Sedative, Hypnotic or Anxiolytic Intoxication (292.89), Sedation, Hypnotic or Anxiolytic Intoxication Delirium (292.81), Sedation, Hypnotic or Anxiolytic Withdrawal Delirium (292.81), Sedation, Hypnotic or Anxiolytic Induced Persisting Dementia (292.82), Sedation, Hypnotic or Anxiolytic-Induced Psychotic Disorder with Delusions (292.11), Sedation, Hypnotic or Anxiolytic-Induced Psychotic Disorder with Hallucinations (292.12), Sedation, Hypnotic or Anxiolytic-Induced Mood Disorder (292.84), Sedation, Hypnotic or Anxiolytic-Induced Anxiety Disorder (292.89), Other (or Unknown) Substance Intoxication (292.89), Other (or Unknown) Substance Induced Delirium (292.81), Other (or Unknown) Substance-Induced Persisting Dementia (292.82), Other (or Unknown) Substance-Induced Psychotic Disorder with Delusions (292.11), Other (or Unknown) Substance-Induced Psychotic Disorder with Hallucinations (292.12), Other (or Unknown) Substance-Induced Mood Disorder (292.84), Other (or Unknown) Substance-Induced Anxiety Disorder (292.89), Other (or Unknown) Substance Disorder Not Otherwise Specified (292.9). Obsessive Compulsive Disorder (300.3), Post-traumatic Stress Disorder (309.81), Generalized Anxiety Disorder (300.02). Anxiety Disorder Not Otherwise Specified (300.00), Body Dysmorphic Disorder (300.7), Hypochondriasis (or Hypochondriacal Neurosis) (300.7), Somatization Disorder (300.81), Undifferentiated Somatoform Disorder (300.81), Somatoform Disorder Not Otherwise Specified (300.81), Intermittent Explosive Disorder (312.34), Kleptomania (312.32), Pathological Gambling (312.31), Pyromania (312.33), Trichotillomania (312.39), and Impulse Control Disorder NOS (312.30), Schizophrenia, Paranoid Type, (295.30), Schizophrenia, Disorganized (295.10), Schizophrenia, Catatonic Type, (295.20), Schizophrenia, Undifferentiated Type (295.90), Schizophrenia, Residual Type (295.60), Schizophreniform Disorder (295.40), Schizoaffective Disorder (295.70), Delusional Disorder (297.1), Brief Psychotic Disorder (298.8), Shared Psychotic Disorder (297.3), Psychotic Disorder Due to a General Medical Condition with Delusions (293.81), Psychotic Disorder Due to a General Medical Condition with Hallucinations (293.82), Psychotic Disorders Not 15 Otherwise Specified (298.9), Major Depression, Single Episode, Severe, without Psychotic Features (296.23), Major Depression, Recurrent, Severe, without Psychotic Features (296.33), Bipolar Disorder, Mixed, Severe, without Psychotic Features (296.63), Bipolar Disorder, Mixed, Severe, with Psychotic Features (296.64), Bipolar Disorder, Manic, Severe, without Psychotic Features (296.43), Bipolar Disorder, Manic, Severe, with Psychotic Features (296.44), Bipolar Disorder, Depressed, Severe, without Psychotic Features (296.53), Bipolar Disorder, Depressed, Severe, with Psychotic Features (296.54), Bipolar II Disorder (296.89), Bipolar Disorder Not Otherwise Specified (296.80), Personality Disorders, Paranoid (301.0), Personality Disorders, Schizoid (301.20), Personality Disorders, Schizotypal (301.22), Personality Disorders, Antisocial (301.7), and Personality Disorders, Borderline (301.83). All of the above indication can be selected out in individual embodiments and can be used in any combination of aspects and embodiments herein.

As used herein the term "substantially no burst" or "substantially burstless" (both terms are used interchangeably in the present description) is intended to mean that upon subcutaneous administration of a paliperidone compound, which may be a prodrug or an active paliperidone compound, the ratio of the peak concentration of a detectable paliperidone compound in blood plasma during the first 48 hours after subcutaneous administration, to the lowest concentration of a detectable paliperidone compound in blood plasma after the peak concentration during the first 48 hours after administration is less than 10, such as less than 5, less than 3 (substantially no burst detectable), preferred less than 2 (no burst detectable), more preferably less than 3.

In respect of detecting a paliperidone in blood plasma, such paliperidone compound may be the paliperidone or in case the paliperidone compound is a prodrug, the detectable paliperidone will be the paliperidone released from the prodrug, such as paliperidone free base.

As used herein the term "peak to trough ratio" is intended to mean the ratio between the highest plasma concentration and the lowest plasma concentration of paliperidone released from a paliperidone compound, within a given period between administrations.

As used herein, the term "steady state" is intended to refer to a pharmacokinetic profile after a third consecutive injection.

As used herein, the term "prodrug" is intended to mean a paliperidone compound that undergoes biotransformation before exhibiting its pharmacological effects. Such prodrugs may be carrier-linked prodrugs containing a temporary linkage of paliperidone with a carrier group that produces improved physicochemical or pharmacokinetic properties and that is easily removed in vivo, usually by a hydrolytic cleavage; such prodrugs may also be cascade-type prodrugs for which the cleavage of the carrier group becomes effective only after unmasking an activating group.

Biotransformation refers to enzyme mediated hydrolysis or autohydrolysis or autocleavage of a chemical bond connecting paliperidone and a promoiety and resulting in the release of free paliperidone in vitro or under in vivo conditions (aqueous buffered solution at pH 7.4, 37° C.).

The linkers employed in such carrier-linked prodrugs may be transient, meaning that they are non-enzymatically hydrolytically degradable (cleavable) under physiological conditions (aqueous buffer at pH 7.4, 37° C.) with half-lives ranging from, for example, one hour to three months.

On the other hand, stable linkages such as employed in connecting backbone moieties and spacer, are typically non-cleavable permanent bonds meaning that the respective spacer or connecting moiety have a half-life of at least six months under physiological conditions (aqueous buffer at pH 7.4, 37° C.).

Suitable carriers are polymers, preferably insoluble crosslinked biodegradable hydrogels and can either be directly conjugated to the linker or via a non cleavable spacer. The terms "paliperidone hydrogel prodrug" and "hydrogel-linked prodrug of paliperidone" refer to carrier-linked prodrugs of paliperidone, wherein the carrier is a hydrogel and both terms are used synonymously. The terms "hydrogel prodrug" and "hydrogel-linked prodrug" refer to prodrugs of biologically active agents transiently linked to a hydrogel and both terms are used synonymously.

In case the biologically active agents; prodrugs, especially hydrogel prodrugs contain one or more acidic or basic groups, the invention also comprises their corresponding pharmaceutically or toxicologically acceptable salts, in particular their pharmaceutically utilizable salts. Thus, the prodrugs which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Prodrugs which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the prodrugs simultaneously contain acidic and basic groups in the molecule, the invention also includes, in addition to the salt forms mentioned, inner salts or betaines (zwitterions). The respective salts of the prodrugs of the present invention can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

As used herein the term "a hydrogel" is intended to mean a three-dimensional, hydrophilic or amphiphilic polymeric network capable of taking up large quantities of water, such as the at least twofold amount of its dry weight. The networks are composed of homopolymers or copolymers, and are insoluble due to the presence of covalent chemical or physical (ionic, hydrophobic interactions, entanglements) crosslinks. The crosslinks provide the network structure and physical integrity. Hydrogels contain hydrophilic moieties which allow them to swell in aqueous media. The chains of the network are connected in such a fashion that pores exist and that a substantial fraction of these pores are of dimensions between 1 nm and 1000 nm.

As used herein the term "a depot" is intended to mean a drug delivery system, administered as a subcutaneous injection, of a paliperidone compound, capable of consistently releasing paliperidone over an extended period of time.

As used herein the term "a peak concentration" is intended to mean the highest concentration obtained after administration of a paliperidone compound.

As used herein the term "Non-active linker" means a linker which does not show the pharmacological effects of paliperidone.

As used herein the term "Alkyl" means a straight-chain (linear, unbranched) or branched carbon chain. Optionally, each hydrogen of an alkyl carbon may be replaced by a substituent as indicated herein.

"$C_{1-4}$ alkyl" means an alkyl chain having 1 to 4 carbon atoms (unsubstituted $C_{1-4}$ alkyl), e.g. if present at the end of a molecule: methyl, ethyl, n-propyl, isopropyl, n-butyl, isobutyl, sec butyl tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(H_3)_2$—, when two moieties of a molecule are linked by the alkyl group (also referred to as $C_{1-4}$ alkylene). Optionally, each hydrogen of a $C_{1-4}$ alkyl carbon may be replaced by a substituent as indicated herein. Accordingly, "$C_{1-50}$ alkyl" means an alkyl chain having 1 to 50 carbon atoms.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl, tert-butyl, n-pentyl, n-hexyl, or e.g. —$CH_2$—, —$CH_2$—$CH_2$—, —$CH(CH_3)$—, —$C(CH_2)$—, —$CH_2$—$CH_2$—$CH_2$—, —$CH(C_2H_5)$—, —$C(CH_3)_2$—, when two moieties of a molecule are linked by the alkyl group (also referred to as $C_{1-6}$ alkylene). Each hydrogen of a $C_{1-6}$ alkyl carbon may be replaced by a substituent as indicated herein. The terms $C_{1-10}$ alkyl or $C_{1-10}$ alkylene are defined accordingly.

"$C_{2-6}$ alkenyl" means an alkenyl chain having 2 to 6 carbon atoms, e.g. if present at the end of a molecule: —$CH$=$CH_2$, —$CH$=$CH$—$CH_3$, —$CH_2$—$CH$=$CH_2$, —$CH$=$CH$—$CH_2$—$CH_3$, —$CH$=$CH$—$CH$=$CH_2$, or e.g. —$CH$=$CH$—, when two moieties of a molecule are linked by the alkenyl group. Each hydrogen of a $C_{2-6}$ alkenyl carbon may be replaced by a substituent as indicated herein. The term $C_{2-4}$ alkenyl is defined accordingly.

"$C_{2-6}$ alkynyl" means an alkynyl chain having 2 to 6 carbon atoms, e.g. if present at the end of a molecule: —$C$≡$CH$, —$CH_2$—$C$≡$CH$, $CH_2$—$CH_2$—$C$≡$CH$, $CH_2$—$C$≡$C$—$CH_3$, or e.g. —$C$≡$C$— when two moieties of a molecule are linked by the alkynyl group. Each hydrogen of a $C_{2-6}$ alkynyl carbon may be replaced by a substituent as indicated herein. The term $C_{2-4}$ alkynyl is defined accordingly.

As used herein the term "$C_{2-50}$ alkenyl" means a branched or unbranched alkenyl chain having 2 to 50 carbon atoms, e.g. if present at the end of a molecule: —$CH$=$CH_2$, —$CH$=$CH$—$CH_3$, —$CH_2$—$CH$=$CH_2$, —$CH$=$CH$—$CH_2$—$CH_3$, —$CH$=$C$—$CH$=$CH_2$, or e.g. —$CH$=$CH$—, when two moieties of a molecule are linked by the alkenyl group. Each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur.

As used herein the term "$C_{2-50}$ alkynyl" means a branched or unbranched alkynyl chain having 2 to 50 carbon atoms, e.g. if present at the end of a molecule: —$C$≡$CH$, —$CH_2$—$C$≡$CH$, $CH_2$—$CH_2$—$C$≡$CH$, $CH_2$—$C$≡$C$—$CH_3$, or e.g. —$C$≡$C$— when two moieties of a molecule are linked by the alkynyl group. Each hydrogen of a $C_{2-50}$ alkynyl carbon may be replaced by a substituent as further specified. Accordingly, the term "alkynyl" relates to a carbon charm with at least one carbon carbon triple bond. Optionally, one or more double bonds may occur.

As used herein the term "$C_{3-7}$ cycloalkyl" or "$C_{3-7}$ cycloalkyl ring" means a cyclic alkyl chain having 3 to 7 carbon atoms, which may have carbon-carbon double bonds being at least partially saturated, e.g. cyclopropyl, cyclobutyl, cyclopentyl, cyclohexyl, cyclohexenyl, cycloheptyl. Each hydrogen of a cycloalkyl carbon may be replaced by a substituent as indicated herein. The term "$C_{3-7}$ cycloalkyl" or "$C_{3-7}$ cycloalkyl ring" also includes bridged bicycles like norbornane or norbornene. Accordingly, "$C_{3-5}$ cycloalkyl" means a cycloalkyl having 3 to 5 carbon atoms.

Accordingly, "$C_{3-10}$ cycloalkyl" means a cyclic alkyl having 3 to 10 carbon atoms, e.g. $C_{3-7}$ cycloalkyl; cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

As used herein the term "Halogen" means fluoro, chloro, bromo or iodo. It is generally preferred that halogen is fluoro or chloro.

As used herein the term "4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"8 to 11 membered heterobicyclyl" or "8 to 11 membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 8 to 11 membered heterobicyclyl). Examples for a 8 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 8 to 11 membered heterobicycle also includes spiro structures of two rings like 1,4-dioxa-8-azaspiro[4.5]decane or bridged heterocycles like 8-aza-bicyclo[3.2.1]octane. The term "9 to 11 membered heterobicyclyl" or "9 to 11 membered heterobicycle".

The term "interrupted" means that between two carbon atoms of, for example, a linker or a spacer or at the respective end of the carbon chain between the respective carbon atom and the hydrogen atom a group (such a —O— or —NH—) is inserted.

As used herein the term the term "pharmaceutically acceptable" means approved by a regulatory agency such as the EMEA (Europe) and/or the FDA (US) and/or any other national regulatory agency for use in animals, preferably in humans.

As used herein the term "pharmaceutical composition" or "composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable excipient (pharmaceutically acceptable carrier).

"Dry composition" means that the paliperidone hydrogel prodrug composition is provided in a dry form in a container. Suitable methods for drying are spray-drying and lyophilization (freeze-drying). Such dry composition of paliperidone hydrogel prodrug has a residual water content of a maximum of 10%, preferably less than 5% and more preferably less than 2% (determined according to Karl Fischer). The preferred method of drying is lyophilization. "Lyophilized composition" means that the paliperidone hydrogel polymer prodrug composition was first frozen and subsequently subjected to water reduction by means of reduced pressure. This terminology does not exclude additional drying steps which occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

"Reconstitution" means the restoration of the composition's condition prior to drying, such as a solution or suspension, by adding a liquid prior to administrating the composition to a patient in need thereof. The liquid may contain one or more excipients.

"Reconstitution solution" refers to the liquid used to reconstitute the dry composition of a paliperidone hydrogel prodrug prior to administration to a patient in need thereof.

"Container" means any container in which the paliperidone hydrogel prodrug composition is comprised and can be stored until reconstitution.

"Buffer" or "buffering agent" refers to chemical compounds that maintain the pH in a desired range. Physiologically tolerated buffers are, for example, sodium phosphate, succinate, histidine, bicarbonate, citrate and acetate, sulphate, nitrate, chloride, pyruvate. Antacids such as Mg(OH)$_2$ or ZnCO$_3$ may be also used. Buffering capacity may be adjusted to match the conditions most sensitive to pH stability.

"Excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions.

A "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as monosodium glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof.

"Surfactant" refers to wetting agents that lower the surface tension of a liquid.

"Isotonicity modifiers" refer to compounds which minimize pain that can result from cell damage due to osmotic pressure differences at the injection depot.

The term "stabilizers" refers to compounds used to stabilize the hydrogel prodrug. Stabilisation is achieved by strengthening of the protein-stabilising forces, by destabilisation of the denatured state, or by direct binding of excipients to the protein.

"Anti-adsorption agents" refers to mainly ionic or non-ionic surfactants or other proteins or soluble polymers used to coat or adsorb competitively to the inner surface of the composition's container. Chosen concentration and type of excipient depend on the effect to be avoided but typically a monolayer of surfactant is formed at the interface just above the CMC value.

"Oxidation protection agents" refers to antioxidants such as ascorbic acid, ectoine, glutathione, methionine, monothioglycerol, morin, polyethylenimine (PEI), propyl gallate, vitamin F, chelating agents such aus citric acid, EDTA, hexaphosphate, thioglycolic acid.

"Antimicrobial" refers to a chemical substance that kills or inhibits the growth of microorganisms, such as bacteria, fungi, yeasts, protozoans and/or destroys viruses.

"Sealing a container" means that the container is closed in such way that it is airtight, allowing no gas exchange between the outside and the inside and keeping the content sterile.

"Free form" of a drug refers to the drug in its unmodified, pharmacologically active form, such as after being released from a polymer conjugate.

The terms "drug", "biologically active molecule", "biologically active moiety", "biologically active agent", "active agent", and the like mean any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals.

A "therapeutically effective amount" of a paliperidone compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

"Stable" and "stability" means that within the indicated storage time the hydrogel conjugates remain conjugated and do not hydrolyze to a substantial extent and exhibit an acceptable impurity profile relating to paliperidone. To be considered stable, the composition contains less than 5% of the drug in its free form, preferably less than 4%, more preferably less than 3% and most preferably less than 2% of the drug in its free form.

As used herein the term "a", "an", and "the" and similar referents are to be construed to cover both the singular and the plural, unless otherwise indicated herein or clearly contradicted by context.

The term "paliperidone" as used herein is intended to mean paliperidone as free base as well as an acid addition salt, typically a pharmaceutically acceptable salt, thereof, and hydrates and solvates thereof, in crystalline or amorphous form. Paliperidone may be present in R-form, S-form or in a mixture of R- and S-form (especially as racemate).

The term "paliperidone compound" as used herein is intended to mean paliperidone formulated or encapsulated in a depot composition or linked to a carrier molecule, e.g. a polymer carrier, such as a prodrug of paliperidone, which prodrugs may also form salts.

The term "immediate onset of action" as used herein is intended to mean that a therapeutically effective amount of the paliperidone is reached in vivo, such as in the human plasma, within a relatively short time period, such as within 30 hours of administration, typically within 24 hours of administration. In a particular embodiment the therapeutic plasma concentration of paliperidone is reached within the first 24 hours after dosing.

The term "continuously for at least 3 weeks" as used herein is intended to mean that paliperidone is released in a subject, such as a human subject, without interruptions from a paliperidone compound and in such a way that the therapeutically effective amount of paliperidone is substantially maintained over 3 weeks or more.

The term "reagent" refers to an intermediate or starting material used in the assembly process leading to a prodrug of the present invention.

The term "chemical functional group" refers to carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine.

If a chemical functional group is coupled to another chemical functional group, the resulting chemical structure is referred to as "linkage". For example, the reaction of an amine group with a carboxyl group results in an amide linkage.

"Reactive functional groups" are chemical functional groups of the backbone moiety, which are connected to the hyperbranched moiety.

"Functional group" is the collective term used for "reactive functional group", "degradable interconnected functional group", or "conjugate functional group".

A "degradable interconnected functional group" is a linkage comprising a biodegradable bond which on one side is connected to a spacer moiety connected to a backbone moiety and on the other side is connected to the crosslinking moiety. The terms "degradable interconnected functional group", "biodegradable interconnected functional group", "interconnected biodegradable functional group" and "interconnected functional group" are used synonymously.

The terms "blocking group" or "capping group" are used synonymously and refer to moieties which are irreversibly connected to reactive functional groups to render them incapable of reacting with for example chemical functional groups.

The terms "protecting group" or "protective group" refers to a moiety which is reversibly connected to reactive functional groups to render them incapable of reacting with for example other chemical functional groups.

The term "interconnectable functional group" refers to chemical functional groups, which participate in a radical polymerization reaction and are part of the crosslinker reagent or the backbone reagent.

The term "polymerizable functional group" refers to chemical functional groups, which participate in a ligation-type polymerization reaction and are part of the crosslinker reagent and the backbone reagent.

A backbone moiety may comprise a spacer moiety which at one end is connected to the backbone moiety and on the other side to the crosslinking moiety.

The term "derivatives" refers to chemical functional groups suitably substituted with protecting and/or activation groups or to activated forms of a corresponding chemical functional group which are known to the person skilled in the art. For example, activated forms of carboxyl groups include but are not limited to active esters, such as succinimidyl ester, benzotriazyl ester, nitrophenyl ester, pentafluorophenyl ester, azabenzotriazyl ester, acyl halogenides, mixed or symmetrical anhydrides, acyl imidazole.

The term "non-enzymatically cleavable linker" refers to linkers that are hydrolytically degradable under physiological conditions without enzymatic activity.

"Non-biologically active linker" means a linker which does not show the pharmacological effects of the drug (D-H) derived from the biologically active moiety.

The terms "spacer", "spacer group", "spacer molecule", and "spacer moiety" are used interchangeably and if used to describe a moiety present in the hydrogel carrier of the invention, refer to any moiety suitable for connecting two moieties, such as $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl.

The terms "terminal", "terminus" or "distal end" refer to the position of a functional group or linkage within a molecule or moiety, whereby such functional group may be a chemical functional group and the linkage may be a degradable or permanent linkage, characterized by being located adjacent to or within a linkage between two moieties or at the end of an oligomeric or polymeric chain.

The phrases "in bound form" or "moiety" refer to substructures which are part of a larger molecule. The phrase "in bound form" is used to simplify reference to moieties by naming or listing reagents, starting materials or hypothetical starting materials well known in the art, and whereby "in bound form" means that for example one or more hydrogen radicals (—H), or one or more activating or protecting groups present in the reagents or starting materials are not present in the moiety.

It is understood that all reagents and moieties comprising polymeric moieties refer to macromolecular entities known to exhibit variabilities with respect to molecular weight, chain lengths or degree of polymerization, or the number of functional groups. Structures shown for backbone reagents, backbone moieties, crosslinker reagents, and crosslinker moieties are thus only representative examples.

A reagent or moiety may be linear or branched. If the reagent or moiety has two terminal groups, it is referred to as a linear reagent or moiety. If the reagent or moiety has more than two terminal groups, it is considered to be a branched or multi-functional reagent or moiety.

The term "poly(ethylene glycol) based polymeric chain" or "PEG based chain" refers to an oligo- or polymeric molecular chain.

Preferably, such poly(ethylene glycol) based polymeric chain is connected to a branching core, it is a linear poly (ethylene glycol) chain, of which one terminus is connected to the branching core and the other to a hyperbranched dendritic moiety. It is understood that a PEG-based chain may be terminated or interrupted by alkyl or aryl groups optionally substituted with heteroatoms and chemical functional groups.

If the term "poly(ethylene glycol) based polymeric chain" is used in reference to a crosslinker reagent, it refers to a crosslinker moiety or chain comprising at least 20 weight % ethylene glycol moieties.

The present invention relates to preparations of long acting paliperidone compounds for subcutaneous administration.

The present inventors have discovered that paliperidone compounds, such as in the form of a depot formulation or a prodrug, can be continuously released for a period of 3 weeks or more from a composition wherein the therapeutic effective plasma concentration is attained within the first 24 hours after subcutaneous injection, or shorter, and without any burst effect. Furthermore, by avoiding a burst of paliperidone the risk of harmful side-effects in a patient is reduced.

The present invention provides a pharmaceutical composition with a profile of dosing once a month or even less frequent, without the need for additional oral or injectable medication.

The present invention reduces the risk of post-injection delirium/sedation syndrome which increases the safety for the patients and reduces health care costs as the need for post injection patient monitoring is reduced.

It is a further object of the current invention to provide a novel paliperidone composition with a reduced need for different needles dimensions for patients with differing body mass index (BMI).

It is a further object of the current invention to provide a long acting paliperidone depot having low variations in peaks and troughs in plasma concentrations.

Further advantages will be apparent when reading the present description.

In one aspect the present invention relates to a pharmaceutical composition for subcutaneous injection comprising a paliperidone compound wherein the composition releases the paliperidone with an immediate onset of action and continuously for at least 3 weeks, and wherein the composition has a pharmacokinetic profile in vivo with substantially no burst release of paliperidone.

In another aspect the present invention relates to a pharmaceutical composition for subcutaneous injection comprising a paliperidone compound of a concentration of at least 10 mg/ml based on quantitative release of free paliperidone from the compound, which composition releases the paliperidone continuously for at least 3 weeks. In one embodiment the paliperidone is released with an immediate onset of action.

In a further embodiment the composition is characterized by releasing the paliperidone in such way that the therapeutic plasma levels of paliperidone are reached within 24 hours of administration, such as within 18 hours of administration, e.g. within 12 hours of administration.

In a still further embodiment the pharmacokinetic profile is measured in mammalian blood plasma, such as human blood plasma. Plasma paliperidone concentrations can be measured with mass spectrometry methods known in the art and by relating the results to a calibration curve obtained from a paliperidone standard. For statistical significance the experiment is run with a suitable number of biological and technical replicates and the mean and median values are calculated to adjust for biological and technical variability.

As used herein a single paliperidone compound dose is given in mg based on quantitative release of free paliperidone from the compound and concentration of a paliperidone compound in a pharmaceutical composition is given in mg/mL based on quantitative release of free paliperidone from the compound. If the paliperidone compound is a prodrug, the concentration is based on quantitative release of free paliperidone from prodrug. By methods well-known in the art, aliquots of a composition are subjected to paliperidone-releasing conditions (aqueous buffer pH 7.4, 37° C., or accelerated conditions at elevated or reduced pH), until no significant increase in paliperidone concentration is observed and the total amount of released paliperidone is determined. It is understood that in the case of soluble carriers, quantitative release is synonymous to quantitative hydrolysis.

DETAILED DESCRIPTION OF EMBODIMENTS

Figure 1:
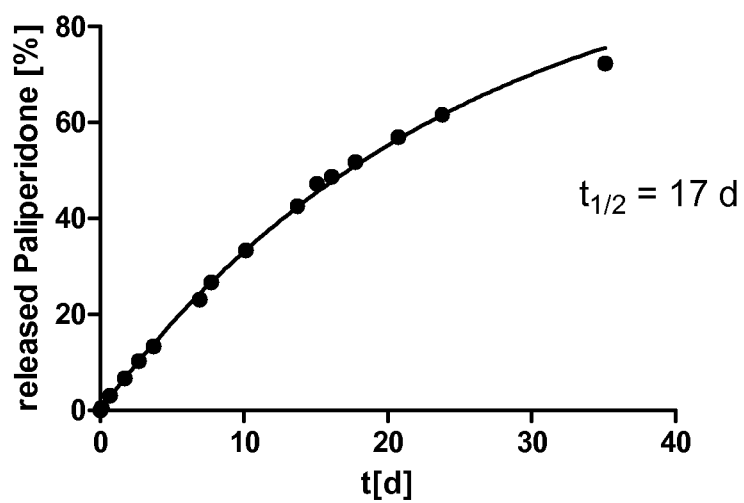
FIG. 1 shows an in vitro degradation/paliperidone release of compound 6a at pH 7.4 and 37° C.

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The above embodiments as well as the embodiments to be described hereunder should be seen as referring to any one of the aspects described herein as well as any one of the embodiments described herein unless it is specified that an embodiment relates to a certain aspect or aspects of the present invention.

In a further embodiment the pharmaceutical composition is characterized by having a pharmacokinetic profile in vivo with no burst release of paliperidone.

In a still further embodiment of the pharmaceutical composition the dosage of the paliperidone compound is at least 10 mg, based on quantitative release of free paliperidone from the compound.

In a further embodiment of the pharmaceutical composition the concentration of the paliperidone compound is at least 10 mg/ml, based on quantitative release of free paliperidone from the compound. In a still further embodiment the composition is characterized by exhibiting a peak to trough ratio of less than 10, such as less than 5, less than 3, or less than 2, preferentially, exhibiting a peak-to-trough ratio at steady state of less than 5, such as less than 4, such as less than 3, or less than 2.

In a further embodiment the pharmaceutical composition is characterized by a continuous release of the paliperidone over the full time period between administrations. Typically, the full time period between administrations (subcutaneous injections) is at least about 3 weeks, such as at least about 4 weeks, e.g. at least 5 weeks. Sometimes it may be preferred to have a continuous release of the paliperidone compound over 6 weeks or more, such as 7 weeks or 8 weeks.

In a still further embodiment the paliperidone compound is a prodrug.

In a further embodiment the paliperidone compound is released from a depot.

The paliperidone compound may be contained in the depot in several ways, for instance the paliperidone compound can be bound in a non-covalent manner or the paliperidone compound is covalently linked to the depot, which depot without limitation is selected from a polymer gel, a hydrogel, or a well hydrated polymer matrix or a biocompatible container.

In a further embodiment paliperidone is released from a depot. Paliperidone may be contained in the depot in several ways, for instance paliperidone can be bound in a non-covalent manner or paliperidone is covalently linked to the depot, which depot without limitation is selected from a polymer gel, a hydrogel, or a well hydrated polymer matrix.

Non-limiting examples for suitable polymers are polymers that are capable of forming quasi-infinite three dimensional well-hydrated molecular networks. Such hydrogels are chemically or physically crosslinked functionalized or non-functionalized polyalkyloxy-based polymers like poly(propylene glycol) or poly(ethylene glycol), dextran, chitosan, hyaluronic acid and derivatives, alginate, xylan, mannan, carrageenan, agarose, cellulose, starch, hydroxyethyl starch (HES) and other carbohydrate based polymers, poly(vinyl alcohols), poly(oxazolines), poly(anhydrides), poly(ortho esters), poly(carbonates), poly(urethanes), poly(acrylic acids), poly(acrylamides) such as poly(hydroxypropyl-methacrylamide) (HMPA), poly(acrylates), poly(methacrylates) like poly(hydroxyethylmethacrylate), poly(organophosphazenes), poly(siloxanes), poly(vinylpyrrolidone), poly(cyanoacrylates), poly(esters) such as poly(lactic acid) or poly(glycolic acids), poly(iminocarbonates), poly(amino acids) such as poly(glutamic acid) or poly lysine, collagen, gelatin, copolymers, grafted copolymers, cross-linked polymers, hydrogels, and block copolymers from the above listed polymers. These polymers may serve as backbone moieties or cross-linking moieties and combination of different polymers as copolymers are possible, provided a high level of hydration of the molecular network. In addition to oligomeric or polymeric cross-linking moieties of the polymer types listed above, low-molecular cross-linking moieties may be used, especially when hydrophilic high-molecular weight backbone moieties are used for the formation of hydrogel prodrug carriers.

Paliperidone can be linked through all relevant functionalities provided by the molecule, typically the preferred functionality is the hydroxyl group of paliperidone.

In an embodiment of the composition, when paliperidone or the compound is bound in a non-covalent manner, paliperidone or the paliperidone compound is fully contained in a depot, typically a polymer gel, such as a hydrogel, e.g. a well hydrated polymer matrix or a biocompatible container.

In another embodiment of the composition, paliperidone or the paliperidone compound is covalently linked in the depot, typically the polymer gel, such as the hydrogel, e.g. the well hydrated polymer matrix.

In a further embodiment of the composition the paliperidone compound is formulated as particles, typically beads, such as particles or beads having a mean diameter of from 1000 µm to 1 µm, such as 500 to 5 µm, such as 300 to 10 µm.

In one particular embodiment, the carrier linked paliperidone prodrug or a pharmaceutically acceptable salt thereof does not contain paliperidone in its free form or as a pharmaceutically acceptable salt thereof, since paliperidone is bound via $X^0$ to a carrier $Z^1$. This means that the carrier linked paliperidone prodrug according to the present invention contain paliperidone as a biologically active moiety. Due to the cleavage of the biological active moiety from the carrier-linked paliperidone prodrugs when administered to a patient in need thereof, paliperidone is released either in its free form or as a pharmaceutically acceptable salt thereof. In other words, the carrier-linked paliperidone prodrugs contain paliperidone, which is substituted with $X^0$, which in turn is covalently bound to a carrier $Z^1$, said carrier comprises a covalently bound pharmaceutically acceptable polymer, preferably a hydrogel, optionally covalently bound through a spacer moiety.

The carrier $Z^1$ comprises a covalently bound pharmaceutically acceptable polymer. The term polymer describes a molecule comprised of repeating structural units connected by chemical bonds in a linear, circular, branched, crosslinked or dendrimeric way or a combination thereof, which can be of synthetic or biological origin or a combination of both. Typically, a polymer has a molecular weight of at least 1 kDa.

Preferred polymers are selected from 2-methacryloyl-oxyethyl phosphoyl cholins, hydrogels, PEG-based hydrogels, poly(acrylic acids), poly(acrylates), poly(acrylamides), poly (alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly (cyanoacrylates), poly(dimethylacrylamides), poly(esters), poly(ethylenes), poly(ethyleneglycols), poly(ethylene oxides), poly(ethyl phosphates), poly(ethyloxazolines), poly (glycolic acids), poly(hydroxyethyl acrylates), poly(hydroxyethyloxazolines), poly(hydroxymethacrylates), poly (hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, mannans, pectins, rhamnogalacturonans, starches, hydroxyalkyl starches, hydroxyethyl starches and other carbohydrate-based polymers, xylans, and copolymers thereof.

As indicated above, the carrier may be a hydrogel (as one option for a polymer) which are known in the art. Suitable hydrogels are described in WO-A 2006/003011 or EP-A 1 625 856. Accordingly, a hydrogel may be defined as a three-dimensional, hydrophilic or amphiphilic polymeric network capable of taking up large quantities of water which causes swelling of the hydrogel in aqueous media. The networks are composed of homopolymers or copolymers and are insoluble due to the presence of covalent chemical or physical (ionic, hydrophobic interactions, entanglements) crosslinks. The crosslinks provide the network structure and physical integrity.

Preferably, the polymer is a biodegradable polyethylene glycol (PEG) based water-insoluble hydrogel. The term "PEG-based" as understood herein is applied to a hydrogel as such or its backbone precursors and means that the mass proportion of PEG chains in the hydrogel or the backbone precursors is at least 10% by weight, preferably at least 25%, based on the total weight of the hydrogel or backbone precursor, respectively. The remainder can be made up of other moieties, such as spacers, oligomers or polymers, such as oligo- or polylysines Moreover the term "water-insoluble" refers to a swellable three dimensionally crosslinked molecular network forming the hydrogel. The hydrogel if suspended in a large surplus of water or aqueous buffer of physiological osmolality may take up a substantial amount of water. e.g. up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

Another aspect of the present invention is a carrier-linked paliperidone prodrug comprising a biodegradable hydrogel of the present invention as carrier, wherein a number of permanent linkages of the backbone moieties exist with a transient prodrug linker to which a biologically active moiety is covalently attached.

The reactive functional groups of a reactive biodegradable hydrogel or modified reactive biodegradable hydrogel serve as attachment points for direct linkage through the before mentioned permanent linkages of paliperidone or paliperidone-linker conjugate. Ideally, the hydrogel-connected drug-linker conjugates are dispersed homogeneously throughout the hydrogel according to the invention, and may or may not be present on the surface of the hydrogel according to the invention.

The functional groups may be attached to a linear chain. In this case, the functional groups may be spaced regularly or irregularly across the chain, or alternatively, the chain may be terminated by two dendritic moieties, providing for the total of functional groups.

Remaining reactive functional groups which are not connected to a transient prodrug linker or to a spacer connected to a transient prodrug linker may be capped with suitable blocking reagents.

Preferably, the covalent attachment formed between the reactive functional groups provided by the backbone moieties and the prodrug linker are permanent bonds. Suitable functional groups for attachment of the prodrug linker to the hydrogel according to the invention include but are not limited to carboxylic acid and derivatives, carbonate and derivatives, hydroxyl, hydrazine, hydroxylamine, maleamic acid and derivatives, ketone, amino, aldehyde, thiol and disulfide.

According to this invention, the biodegradable hydrogel according to the invention is composed of backbone moieties interconnected by hydrolytically degradable bonds.

In a hydrogel carrying drug-linker conjugates according to the invention, a backbone moiety is characterized by a number of functional groups, comprising interconnected biodegradable functional groups and hydrogel-connected drug-linker conjugates, and optionally capping groups. This means that a backbone moiety is characterized by a number of hydrogel-connected drug-linker conjugates; functional groups, comprising biodegradable interconnected functional groups; and optionally capping groups. Preferably, the sum of interconnected biodegradable functional groups and drug-linker conjugates and capping groups is 16-128, preferred 20-100, more preferred 24-80 and most preferred 30-60.

Preferably, the sum of interconnected functional groups and hydrogel-connected drug-linker conjugates and capping groups of a backbone moiety is equally divided by the number of PEG-based polymeric chains extending from the branching core. For instance, if there are 32 interconnected functional groups anti hydrogel-connected drug-linker conjugates and capping groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups and hydrogel-connected drug-linker conjugates and capping groups per PEG-based polymeric chain is kept to a minimum.

In such carrier-linked prodrugs according to the invention, it is desirable that almost all drug release (>90%) has occurred before a significant amount of release of the backbone moieties (<10%) has taken place. This can be achieved by adjusting the carrier-linked prodrug's half-life versus the degradation kinetics of the hydrogel according to the invention.

Preferentially, a backbone moiety is characterized by having a branching core, from which at least three PEG-based polymeric chains extend. Accordingly, in a preferred aspect of the present invention the backbone reagent comprises a branching core, from which at least three PEG-based polymeric chains extend. Such branching cores may be comprised of poly- or oligoalcohols in bound form, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be comprised of poly- or oligoamines such as ornithine, diaminobutyric acid, trilysine, tetralysine, pentalysine, hexylysine, heptalysine, octalysine, nonalysine, decalysine, undecalysine, dodecalysine, tridecalysine, tetradecalysine, pentadecalysine or oligolysines, polyethyleneimines, polyvinylamines in bound form.

Preferably, the branching core extends three to sixteen PEG-based polymeric chains, more preferably four to eight. Preferred branching cores may be comprised of pentaerythritol, ornithine, diaminobutyric acid, trilysine, tetralysine, pentalysine, hexalysine, heptalysine or oligolysine, low-molecular weight PEI, hexaglycerine, tripentaerythritol in bound form. Preferably, the branching core extends three to sixteen PEG-based polymeric chains, more preferably four to eight.

Preferably, a PEG-based polymeric chain is a linear poly (ethylene glycol) chain, of which one end is connected to the branching core and the other to a hyperbranched dendritic moiety. It is understood that a polymeric PEG-based chain may be terminated or interrupted by alkyl or aryl groups optionally substituted with heteroatoms and chemical functional groups.

Preferably, a PEG-based polymeric chain is a suitably substituted polyethylene glycol derivative (PEG based).

Preferred structures for corresponding PEG-based polymeric chains extending from a branching core contained in a backbone moiety are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), Sarin PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 1 kDa to 15 kDa and even more preferably 1 kDa to 10 kDa.

It is understood that the terminal amine groups of the above mentioned multi-arm molecules are present in bound form in the backbone moiety to provide further interconnected functional groups and reactive functional groups of a backbone moiety.

It is preferred that the sum of interconnected functional groups and reactive functional groups of a backbone moiety is equally divided by the number of PEG-based polymeric chains extending from the branching core. If the number of PEG based polymeric chains extending from the branching core does not allow for an equal distribution, it is preferred that the deviation from the mean number of the sum of interconnected and reactive functional groups per PEG-based polymeric chain is kept to a minimum.

More preferably, the sum of interconnected and reactive functional groups of a backbone moiety is equally divided by the number of PEG-based polymeric chains extending from the branching core. For instance, if there are 32 interconnected functional groups and reactive functional groups, eight groups may be provided by each of the four PEG based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

Such additional functional groups may be provided by dendritic moieties. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties are comprised of trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine in bound form. Examples for such preferred dendritic moieties are comprised of trilysine, tetralysine, pentalysine, hexylysine, heptalysine in bound form, most preferred trilysine, pentalysine or heptalysine, ornithine, diaminobutyric acid in bound form.

Most preferably, the hydrogel carrier of the present invention is characterized in that the backbone moiety has a quarternary carbon of formula C(A-Hyp)$_4$, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four functional groups representing the interconnected functional groups and reactive functional groups.

Preferably, each A is independently selected from the formula —(CH$_2$)$_{n1}$(OCH$_2$CH$_2$)$_n$X—, wherein n1 is 1 or 2; n is an integer in the range of from 5 to 50; and X is a chemical functional group covalently linking A and Hyp.

Preferably, A and Hyp are covalently linked by an amide linkage.

Preferably, the dendritic moiety Hyp is a hyperbranched polypeptide. Preferably, the hyperbranched polypeptide comprises lysine in bound form. Preferably, each dendritic moiety Hyp has a molecular weight in the range of from 0.4 kDa to 4 kDa. It is understood that a backbone moiety C(A-Hyp)$_4$ can consist of the same or different dendritic moieties Hyp and that each Hyp can be chosen independently. Each moiety Hyp consists of between 5 and 32 lysines, preferably of at least 7 lysines, i.e. each moiety Hyp is comprised of between 5 and 32 lysines in bound form, preferably of at least 7 lysines in bound form. Most preferably Hyp is comprised of heptalysinyl.

The reaction of polymerizable functional groups a backbone reagent, more specifically of Hyp with the polymerizable functional groups of polyethyleneglycol based crosslinker reagents results in a permanent amide bond.

Preferably, C(A-Hyp)$_4$ has a molecular weight in the range of from 1 kDa to 20 kDa, more preferably 1 kDa to 15 kDa and even more preferably 1 kDa to 10 kDa.

One preferred backbone moiety is shown below, dashed lines indicate interconnecting biodegradable linkages to crosslinker moieties and n is an integer of from 5 to 50:

Biodegradability of the hydrogels according to the present invention is achieved by introduction of hydrolytically degradable bonds.

The terms "hydrolytically degradable", "biodegradable" or "hydrolytically cleavable", "auto-cleavable", or "self-cleavage", "self-cleavable", "transient" or "temporary" refers within the context of the present invention to bonds and linkages which are non-enzymatically hydrolytically degradable or cleavable under physiological conditions (aqueous buffer at pH 7.4, 37° C.) with half-lives ranging from one hour to three months, including, but are not limited to, aconityls, acetals, amides, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like, preferably aconityls, acetals, carboxylic anhydrides, esters, imines, hydrazones, ortho esters, phosphoesters, phosphosilyl esters, silyl esters, sulfonic esters, aromatic carbamates.

If present in a hydrogel according to the invention as degradable interconnected functional group, preferred biodegradable linkages are esters, carbonates, phosphoesters and sulfonic acid esters and most preferred are esters or carbonates.

Permanent linkages are non-enzymatically hydrolytically degradable under physiological conditions (aqueous buffer at pH 7.4, 37° C.) with half-lives of six months or longer, such as, for example, amides.

To introduce the hydrolytically cleavable bonds into the hydrogel carrier of the invention, the backbone moieties can be directly linked to each other by means of biodegradable bonds.

In one embodiment, the backbone moieties of the biodegradable hydrogel carrier may be linked together directly, i.e. without crosslinker moieties. The hyperbranched dendritic moieties of two backbone moieties of such biodegradable hydrogel may either be directly linked through an interconnected functional group that connects the two hyperbranched dendritic moieties. Alternatively, two hyperbranched den-

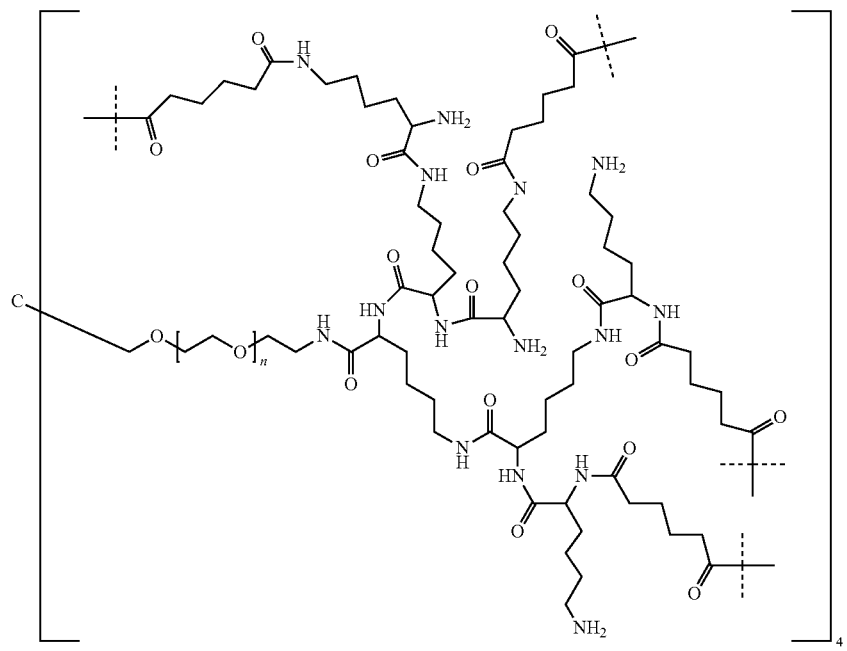

dritic moieties of two different backbone moieties may be interconnected through two spacer moieties connected to a backbone moiety and on the other side connected to a crosslinking moiety separated by interconnected functional groups.

Alternatively, backbone moieties may be linked together through crosslinker moieties, each crosslinker moiety is terminated by at least two of the hydrolytically degradable bonds. In addition to the terminating degradable bonds, the crosslinker moieties may contain further biodegradable bonds. Thus, each end of the crosslinker moiety linked to a backbone moiety comprises a hydrolytically degradable bond, and additional biodegradable bonds may optionally be present in the crosslinker moiety.

Preferably, the biodegradable hydrogel carrier is composed of backbone moieties interconnected by hydrolytically degradable bonds and the backbone moieties are linked together through crosslinker moieties.

The biodegradable hydrogel carrier may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

If present in a hydrogel according to the invention as degradable interconnected functional group, preferred biodegradable linkages are carboxylic esters, carboxylic anhydrides, carbonates, phosphoesters and sulfonic acid esters; more preferably carboxylic esters, carbonates, phosphoesters and sulfonic acid esters and most preferred are carboxylic esters or carbonates.

Preferably, crosslinker moieties have a molecular weight in the range of from 60 Da to 5 kDa, more preferably, from 0.5 kDa to 4 kDa, even more preferably from 1 kDa to 4 kDa, even more preferably from 1 kDa to 3 kDa. In one embodiment, a crosslinker moiety consists of a polymer.

In addition to oligomeric or polymeric crosslinking moieties, low-molecular weight crosslinking moieties may be used, especially when hydrophilic high-molecular weight backbone moieties are used for the formation of a biodegradable hydrogel according to the invention.

Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each m ethylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

If used in reference to a crosslinker moiety or a PEG-based polymeric chain connected to a branching core, the term "PEG-based" refers to a crosslinker moiety or PEG-based polymeric chain comprising at least 20 weight %, ethylene glycol moieties.

In one embodiment, monomers constituting the polymeric crosslinker moieties are connected by biodegradable bonds. Such polymeric crosslinker moieties may contain up to 100 biodegradable bonds or more, depending on the molecular weight of the crosslinker moiety and the molecular weight of the monomer units. Examples for such crosslinker moieties are poly(lactic acid) or poly(glycolic acid) based polymers. It is understood that such poly(lactic acid) or poly(glycolic acid) chain may be terminated or interrupted by alkyl or aryl groups and that they may optionally be substituted with heteroatoms and chemical functional groups.

Preferably, the crosslinker moieties are PEG based, preferably represented by only one PEG based molecular chain. Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

In a preferred embodiment of the present invention the crosslinker moiety consists of PEG, which is symmetrically connected through ester bonds to two alpha, omega-aliphatic dicarboxylic spacers provided by backbone moieties connected to the hyperbranched dendritic moiety through permanent amide bonds.

The dicarboxylic acids of the spacer moieties connected to a backbone moiety and on the other side is connected to a crosslinking moiety consist of 3 to 12 carbon atoms, most preferably between 5 and 8 carbon atoms and may be substituted at one or more carbon atom. Preferred substituents are alkyl groups, hydroxyl groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

Preferably, there is a permanent amide bond between the hyperbranched dendritic moiety and the spacer moiety connected to a backbone moiety and on the other side is connected to a crosslinking moiety.

One preferred crosslinker moiety is shown below; dashed lines indicate interconnecting biodegradable linkages to backbone moieties:

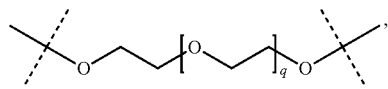

wherein q is an integer of from 5 to 50.

Preferably, the hydrogel carrier is composed of backbone moieties interconnected by hydrolytically degradable bonds.

More preferably, the backbone moieties comprise a branching core of the following formula:

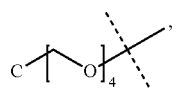

wherein the dashed line indicates attachment to the remainder of the backbone moiety.

More preferably, the backbone moieties comprise a structure of the following formula:

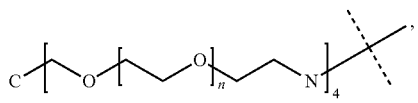

wherein n is an integer of from 5 to 50 and the dashed line indicates attachment to the remainder of the backbone moiety.

Preferably, backbone moiety comprises a hyperbranched moiety Hyp.

More preferably, the backbone moiety comprises a hyperbranched moiety Hyp of the following formula:

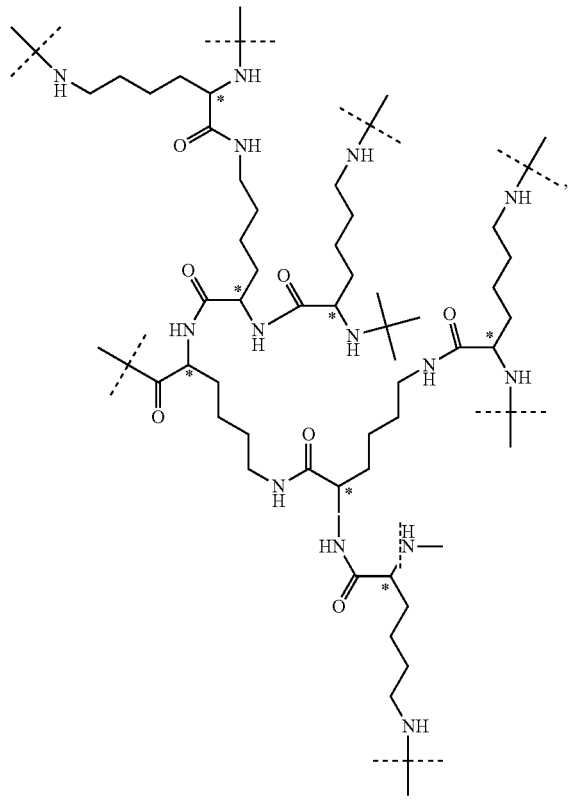

wherein the dashed lines indicate attachment to the rest of the molecule and carbon atoms marked with asterisks indicate in a preferred embodiment S-configuration. However, it is understood that hyperbranched moieties Hyp as shown above may also be in R-confirmation or may be racemic.

Preferably, the backbone moieties are attached to at least one spacer of the following formula:

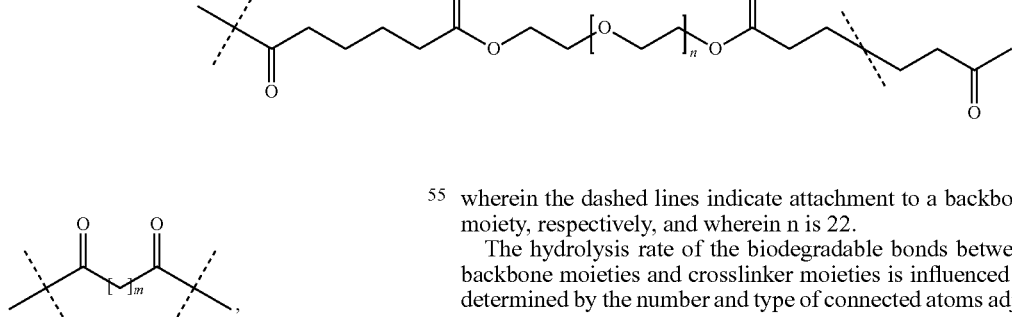

wherein one of the dashed lines indicates attachment to the hyperbranched moiety Hyp and the second dashed line indicates attachment to the rest of the molecule; and wherein m is an integer of from 2 to 4.

Preferably, the backbone moieties are linked together through crosslinker moieties having the following structure

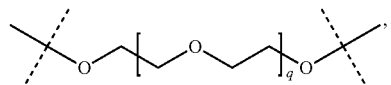

wherein q is an integer from 3 to 100;

Preferably, $Z^0$ is of the following formula:

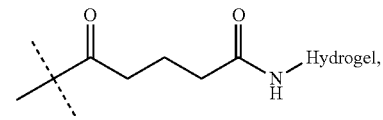

wherein the dashed line indicates attachment to paliperidone; and wherein the backbone moieties of the hydrogel are linked together through moieties of the following formula:

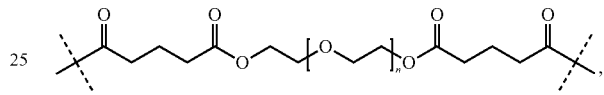

wherein the dashed lines indicate attachment to a backbone moiety, respectively, and wherein n is 45.

In an alternative preferred embodiment, $Z^0$ is of the following formula:

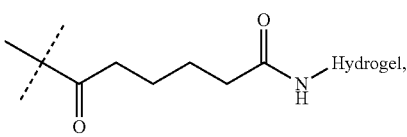

wherein the dashed line indicates attachment to paliperidone; and wherein the backbone moieties of the hydrogel are linked together through moieties of the following formula:

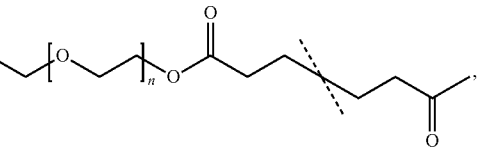

wherein the dashed lines indicate attachment to a backbone moiety, respectively, and wherein n is 22.

The hydrolysis rate of the biodegradable bonds between backbone moieties and crosslinker moieties is influenced or determined by the number and type of connected atoms adjacent to the PEG-ester carboxy group. For instance, by selecting from succinic, adipic or glutaric acid for PEG ester formation it is possible to vary the degradation half-lives of the biodegradable hydrogel carrier according to the invention.

The degradation of the biodegradable hydrogel carrier according to the invention is a multi-step reaction where a multitude of degradable bonds is cleaved resulting in degradation products which may be water-soluble or water-insoluble. However, water-insoluble degradation products may further comprise degradable bonds so that they can be cleaved in that water-soluble degradation products are obtained. These water-soluble degradation products may comprise one or more backbone moieties. It is understood that released backbone moieties may, for instance, be permanently conjugated to spacer or blocking or linker groups or affinity groups and/or prodrug linker degradation products and that also water-soluble degradation products may comprise degradable bonds.

The structures of the branching core, PEG-based polymeric chains, hyperbranched dendritic moieties and moieties attached to the hyperbranched dendritic moieties can be inferred from the corresponding descriptions provided in the sections covering the hydrogel carriers of the present invention. It is understood that the structure of a degradant depends on the type of hydrogel according to the invention undergoing degradation.

The total amount of backbone moieties can be measured in solution after complete degradation of the hydrogel according to the invention, and during degradation, fractions of soluble backbone degradation products can be separated from the insoluble hydrogel according to the invention and can be quantified without interference from other soluble degradation products released from the hydrogel according to the invention. A hydrogel object according to the invention may be separated from excess water of buffer of physiological osmolality by sedimentation or centrifugation. Centrifugation may be performed in such way that the supernatant provides for at least 10% of the volume of the swollen hydrogel according to the invention. Soluble hydrogel degradation products remain in the aqueous supernatant after such sedimentation or centrifugation step, and water-soluble degradation products comprising one or more backbone moieties are detectable by subjecting aliquots of such supernatant to suitable separation and/or analytical methods.

Preferably, water-soluble degradation products may be separated from water insoluble degradation products by filtration through 0.45 μm filters, after which the water soluble degradation products can be found in the flow-through. Water-soluble degradation products may also be separated from water-insoluble degradation products by a combination of a centrifugation and a filtration step.

For instance the backbone moieties may carry groups that exhibit UV absorption at wavelengths where other degradation products do not exhibit UV absorption. Such selectively UV-absorbing groups may be structural components of the backbone moiety such as amide bonds or may be introduced into the backbone by attachment to its reactive functional groups by means of aromatic ring systems such as indoyl groups.

In such hydrogel-linked paliperidone prodrugs according to the invention, it is desirable that almost all paliperidone release (>90%) has occurred before a significant amount of release of the backbone degradation products (<10%) has taken place. This can be achieved by adjusting the hydrogel-linked paliperidone prodrug's half-life versus the hydrogel degradation kinetics.

Optionally, there is a spacer moiety between the carrier and the linker. Preferably, the spacer is connected to the carrier and the linker via stable bonds, such as amide or thiosuccinimide bonds, and preferably these stable bonds are amide bonds. Any spacer known to a person skilled in the art can be used. Preferably, the spacer is a fragment selected from $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl.

The invention preferably covers carrier linked prodrugs of paliperidone according to formula (I):

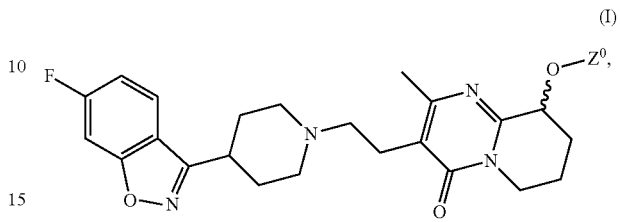

(I)

wherein $Z^0$ is C(O)—$X^0$—$Z^1$; C(O)—X0-$Z^1$; S(O)$_3$—$X^0$—$Z^1$; C(S)—$X^0$—$Z^1$; S(O)$_2$O—$X^0$—$Z^1$; S(O)$_2$N($R^1$)—$X^0$—$Z^1$; CH(O$R^1$)—$X^0$—$Z^1$; C(O$R^1$)(O$R^2$)—$X^0$—$Z^1$; C(O)N($R^1$)—$X^0$—$Z^1$; P(=O)(OH)O—$X^0$—$Z^1$; P(=O)(O$R^1$)O—$X^0$—$Z^1$; P(=O)(SH)O—$X^0$—$Z^1$; P(=O)(S$R^1$)O—$X^0$—$Z^1$; P(=O)(O$R^1$)—$X^0$—$Z^1$; P(=S)(OH)O—$X^0$—$Z^1$; P(=S)(O$R^1$)O—$X^0$—$Z^1$; P(=S)(OH)N($R^1$)—$X^0$—$Z^1$; P(=S)(O$R^1$)N($R^2$)—$X^0$—$Z^1$; P(=O)(OH)N($R^1$)—$X^0$—$Z^1$; or P(=O)(O$R^1$)N($R^2$)—$X^0$—$Z^1$;

$R^1$, $R^2$ are independently selected from the group consisting of $C_{1-6}$ alkyl; or $R^1$, $R^2$ jointly form a $C_{1-6}$ alkylene bridging group;

$X^0$ is $(X^{0A})_{m1}$—$(X^{0B})_{m2}$;

m1; m2 are independently 0; or 1;

$X^{0A}$ is $T^0$;

$X^{0B}$ is a branched or unbranched $C_{1-10}$ alkylene group which is unsubstituted or substituted with one or more $R^3$, which are the same or different;

$R^3$ is halogen; CN; C(O)$R^4$; C(O)O$R^4$; O$R^4$; C(O)$R^4$; C(O)N($R^4R^{4a}$); S(O)$_2$N($R^4R^{4a}$); S(O)N($R^4R^{4a}$); S(O)$_2R^4$; S(O)$R^4$; N($R^4$)S(O)$_2$N($R^{4a}R^{4b}$); S$R^4$; N($R^4R^{4a}$); NO$_2$; OC(O)$R^4$; N($R^4$)C(O)$R^{4a}$; N($R^4$)SO$_2R^{4a}$; N($R^4$)S(O)$R^{4a}$; N($R^4$)C(O)N($R^{4a}R^{4b}$); N($R^4$)C(O)O$R^{4a}$; OC(O)N($R^4R^{4a}$); or $T^0$;

$R^4$, $R^{4a}$, $R^{4b}$ are independently selected from the group consisting of H; $T^0$; $C_{1-4}$ alkyl; $C_{2-4}$ alkenyl; and $C_{2-4}$ alkynyl, wherein $C_{1-4}$ alkyl; $C_{2-4}$ alkenyl; and $C_{2-4}$ alkynyl are optionally substituted with one or more $R^5$, which are the same of different;

$R^5$ is halogen; CN; C(O)$R^6$; C(O)O$R^6$; O$R^6$; C(O)$R^6$; C(O)N($R^6R^{6a}$); S(O)$_2$N($R^6R^{6a}$); S(O)N($R^6R^{6a}$); S(O)$_2R^6$; S(O)$R^6$; N($R^6$)S(O)$_2$N($R^{6a}R^{6b}$); S$R^6$; N($R^6R^{6a}$); NO$_2$; OC(O)$R^6$; N($R^6$)C(O)$R^{6a}$; N($R^6$)SO$_2R^{6a}$; N($R^6$)S(O)$R^{6a}$; N($R^6$)C(O)N($R^{6a}R^{6b}$); N($R^6$)C(O)O$R^{6a}$; OC(O)N($R^6R^{6a}$);

$R^6$, $R^{6a}$, $R^{6b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;

$T^0$ is phenyl; naphthyl; azulenyl; indenyl; indanyl; $C_{3-7}$ cycloalkyl; 3 to 7 membered heterocyclyl; or 8 to 11 membered heterobicyclyl, wherein $T^0$, is optionally substituted with one or more $R^7$, which are the same or different;

$R^7$ is halogen; CN; COO$R^8$; O$R^8$; C(O)$R^8$; C(O)N($R^8R^{8a}$); S(O)$_2$N($R^8R^{8a}$); S(O)N($R^8R^{8a}$); S(O)$_2R^8$; S(O)$R^8$; N($R^8$)S(O)$_2$N($R^8R^{8b}$); S$R^8$; N($R^8R^{8a}$); NO$_2$; OC(O)$R^8$;

N($R^8$)C(O)$R^{8a}$; N($R^8$)S(O)$_2$$R^{8a}$; N($R^8$)S(O)$R^{8a}$; N($R^8$)C(O)O$R^{8a}$; N($R^8$)C(O)N($R^{8a}$$R^{8b}$); OC(O)N($R^8$$R^{8a}$); oxo (=O), where the ring is at least partially saturated; $C_{1-6}$ alkyl; $C_{2-6}$ alkenyl; or $C_{1-6}$ alkynyl, wherein $C_{1-6}$ alkyl; $C_{2-6}$ alkenyl; and $C_{2-6}$ alkynyl are optionally substituted with one or more $R^9$, which are the same or different;

$R^8$, $R^{8a}$, $R^{8b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{10}$, which are the same of different;

$R^9$, $R^{10}$ are independently selected from the group consisting of halogen; CN; C(O)$R^{11}$; C(O)O$R^{11}$; O$R^{11}$; C(O)$R^{11}$; C(O)N($R^{11}$$R^{11a}$); S(O)$_2$N($R^{11}$$R^{11a}$); S(O)N($R^{11}$$R^{11a}$); S(O)$_2$$R^{11}$; S(O)$R^{11}$; N($R^{11}$)S(O)$_2$N($R^{11a}$$R^{11b}$); S$R^{11}$; N($R^{11}$$R^{11a}$); NO$_2$; OC(O)$R^{11}$; N($R^{11}$)C(O)$R^{11a}$; N($R^{11}$)SO$_2$$R^{11a}$; N($R^{11}$)S(O)$R^{11a}$; N($R^{11}$)C(O)N($R^{11a}$$R^{11b}$); N($R^{11}$)C(O)O$R^{11a}$; and OC(O)N($R^{11}$$R^{11a}$);

$R^{11}$, $R^{11a}$, $R^{11b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;

$Z^1$ is a carrier comprising a covalently bound pharmaceutically acceptable polymer, wherein the carrier is covalently attached to $X^0$.

Preferably, $Z^0$ is C(O)—$X^0$—$Z^1$; C(O)O—$X^0$—$Z^1$; or S(O)$_2$—$X^0$—$Z^1$. More preferably, $Z^0$ is C(O)—$X^0$—$Z^1$; or C(O)O—$X^0$—$Z^1$. Even more preferably, $Z^0$ is C(O)—$X^0$—$Z^1$.

Preferably, $X^0$ is unsubstituted.

Preferably, m1 is 0 and m2 is 1.

Preferably, $X^0$—$Z^1$ is C($R^1$$R^2$)CH$_2$—$Z^1$, wherein $R^1$, $R^2$ are independently selected from the group consisting of H and $C_{1-4}$ alkyl, provided that at least one of $R^1$, $R^2$ is other than H; or (CH$_2$)$_n$—$Z^1$, wherein n is 2, 3, 4, 5, 6, 7 or 8, preferably 3, 4, 5, 6, 7 or 8.

Preferably, the carrier $Z^1$ is covalently attached to $X^0$ via amide group.

Another subject of the present invention is a method for the synthesis of a prodrug or a pharmaceutically acceptable salt thereof as defined above. Prodrugs or precursors of prodrugs according to the present invention may be prepared by known methods or in accordance with the reaction sequences described below. The starting materials used in the preparation (synthesis) of prodrugs of the invention or precursors thereof are known or commercially available, or can be prepared by known methods or as described below.

All reactions for the synthesis of the prodrugs according to the present invention including precursors are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a prodrug or a precursor thereof, it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the prodrugs or precursors can be purified by customary purification procedures, for example by recrystallization or chromatography.

The prodrugs according to the present invention (or a pharmaceutically acceptable salt thereof) may be prepared by a method comprising the step of reacting a prodrug precursor L-Y with paliperidone (Pal) to obtain a paliperidone linker conjugate Pal-L by forming a bond OC(O); OC(O)O; OS(O)$_2$; O(O)C(S); OS(O)$_2$O; OS(O)$_2$N($R^1$); OCH(O$R^1$); OC(O$R^1$)(O$R^2$); OC(O)N($R^1$); OP(=O)(OH)O; OP(=O)(O$R^1$)O; OP(=O)(SH)O; OP(=O)(S$R^1$)O; OP(=O)(O$R^1$); OP(=S)(OH)O; OP(=S)(O$R^1$)O; OP(=S)(OH)N($R^1$); OP(=S)(O$R^1$)N($R^2$); OP(=O)(OH)N($R^1$); or OP(=O)(O$R^1$)N($R^2$), wherein Y is a leaving group. Afterwards, Pal-L may be bound to the PEG based hydrogel to obtain the PEG-based hydrogel linked prodrugs Pal-$Z^0$ according to the present invention. Alternatively, the carrier may already be bound to L-Y (as defined below).

In a preferable method of preparation, Pal-L is generated through reaction of a cyclic carboxylic anhydride with paliperidone.

Y is a leaving group. Such leaving groups are known to a person skilled in the art. Preferably, Y is chloride, bromide, fluoride, carboxy, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, N-hydroxysulfosuccinimidyl, or 1-cyano-2-ethoxy-oxoethylidenaminooxy; more preferably Y is chloride, bromide, fluoride, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, or N-hydroxysulfosuccinimidyl.

In case the synthesis of a prodrug according to the present invention is carried out by employing a precursor $L^1$-Y, a paliperidone linker intermediate ($L^1$-Pal) is obtained by reacting $L^1$-Y with the biologically active drug paliperidone (by forming a bond as indicated above). In such a case, said paliperidone intermediate $L^1$-Pal is reacted further to obtain the carrier linked paliperidone product by adding the moiety $L^2$ and the carrier to said paliperidone linker intermediate $L^1$-Pal. It has to be indicated that the addition of $L^2$ and/or the carrier to $L^1$-Pal may be performed in several steps by preparing further intermediate compounds prior to obtaining the prodrug according to the present invention.

Alternatively, a prodrug precursor L*-Y may be employed instead of $L^1$-Y, wherein L' is selected from a fragment of $L^1$, $L^1$ containing at least one protecting group or $L^1$ additionally containing precursors of $L^2$ and/or the carrier.

In the following, possible methods of preparing the carrier linked paliperidone prodrugs according to the present invention or intermediates/precursors thereof are explained in more detail.

The hydrogel linked paliperidone prodrug of the present invention can be prepared starting from the hydrogel of the present invention by convenient methods known in the art. It is clear to a practitioner in the art that several routes exist. For example the prodrug linker mentioned above to which the biologically active moiety is covalently attached can be reacted with the reactive functional groups of the hydrogel of the present invention with or with already bearing the active moiety in part or as whole.

In a preferable method of preparation, the hydrogel is generated through chemical ligation reactions. The hydrogel may be formed from two macromolecular educts with complementary functionalities which undergo a reaction such as a condensation or addition. One of these starting materials is a crosslinker reagent with at least two identical functional groups and the other starting material is a homomultifunctional backbone reagent. Suitable functional groups present on the crosslinker reagent include terminal amino, carboxylic acid and derivatives, maleimide and other alpha,beta unsaturated Michael acceptors like vinylsulfone, thiol, hydroxyl groups. Suitable functional groups present in the backbone reagent include but are not limited to amino, carboxylic acid and derivatives, maleimide and other alpha,beta unsaturated Michael acceptors like vinylsulfone, thiol, hydroxyl groups.

If the crosslinker reagent reactive functional groups are used substoichiometrically with respect to backbone reactive functional groups, the resulting hydrogel will be a reactive hydrogel with free reactive functional groups attached to the backbone structure.

Optionally, the prodrug linker may be first conjugated to paliperidone and the resulting paliperidone-prodrug linker conjugate may then react with the hydrogel's reactive functional groups. Alternatively, after activation of one of the functional groups of the prodrug linker, the linker hydrogel conjugate may be contacted with paliperidone in the second reaction step and excess paliperidone may be removed by filtration after conjugation of the paliperidone to the hydrogel-bound prodrug linker.

Preferably, paliperidone is conjugated to the prodrug linker first and then an activated paliperidone linker conjugate is conjugated to the functional group or groups of a multi-functional moiety (see below for explanation). Preferably, the multi-functional moiety is lysine and the stoicheometry is two activated paliperidone-linker conjugates per lysine moiety. This (paliperidone-linker)$_2$-lysine conjugate is activated and then coupled to the reactive functional groups of the polymerized hydrogel which may already contain multi-functional moieties.

A preferred process for the preparation of a prodrug according to the present invention is as follows:

A preferred starting material for the backbone reagent synthesis is a 4-arm PEG tetra amine or 8-arm PEG octa amine, with the PEG reagent having a molecular weight ranging from 2000 to 10000 Dalton, most preferably from 2000 to 5000 Da. To such multi-arm PEG-derivatives, lysine residues are coupled sequentially to form the hyperbranched backbone reagent. It is understood that the lysines can be partially or fully protected by protective groups during the coupling steps and that also the final backbone reagent may contain protective groups. A preferred building block is bis-boc lysine. Alternatively, instead of sequential additions of lysine residues, a dendritic poly-lysine moiety may be assembled first and subsequently coupled to the 4-arm PEG tetra amine or 8-arm PEG octa amine. It is desirable to obtain backbone reagent carrying 32 amino groups, consequently seven lysines would be attached to each arm of a 4-arm PEG, or five lysines would be attached to each arm of a 8-arm PEG. In another embodiment, the multi-arm PEG derivative is a tetra- or octa carboxy PEG. In this case, the dendritic moieties may be generated from glutaric or aspartic acid, and the resulting backbone reagent would carry 32 carboxy groups. It is understood that all or a fraction of the backbone reagent's functional groups may be present in a free form, as salts or conjugated to protecting groups. It is understood that due to practical reasons the backbone reagent's number of lysines per PEG-arm will be between six and seven, more preferably approximately seven.

A preferred backbone reagent is shown below:

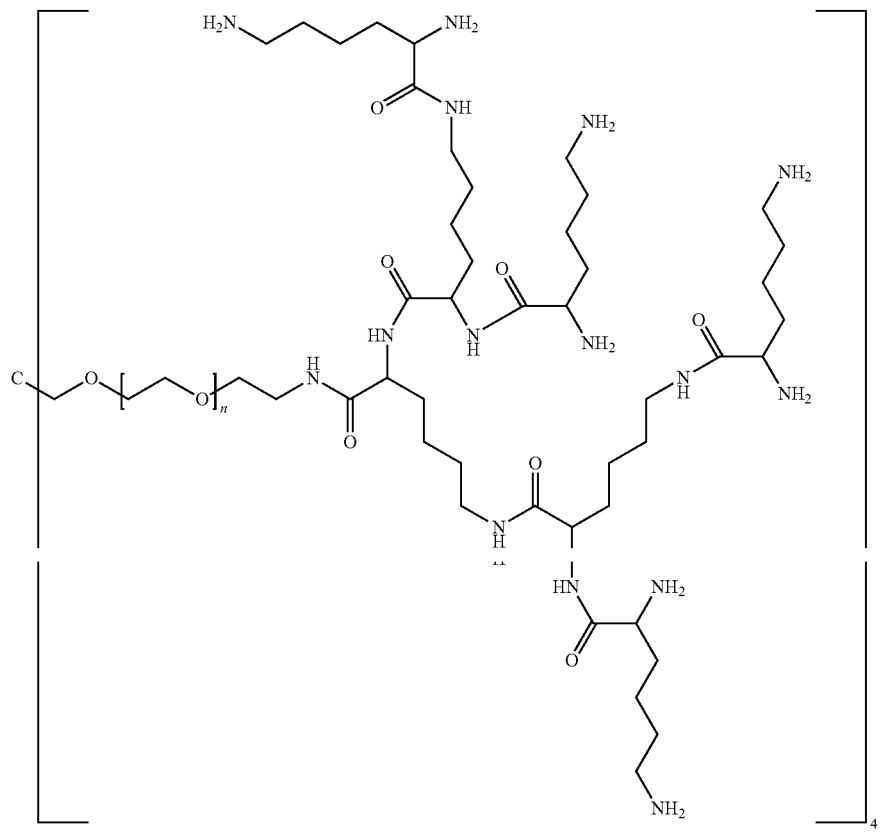

Synthesis of the crosslinker reagent starts from a linear PEG chain with a molecular weight ranging from 0.2 to 5 kDa, more preferably from 0.6 to 2 kDa, which is esterified with a half ester of a dicarboxylic acid, most adipic acid or glutaric acid. Preferred protecting group for half ester formation is the benzylic group. The resulting bis dicarboxylic acid PEG half esters are converted into more reactive carboxy compounds such as acyl chlorides or active esters, eg pentafluorophenyl or N-hydroxysuccinimide esters, most preferred N-hydroxysuccinimide esters, of which preferred selected structure is shown below:

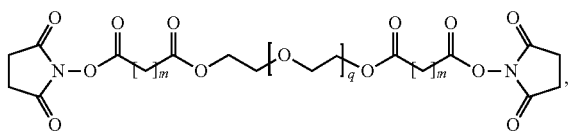

wherein each m independently is an integer ranging from 2 to 4, and
q is an integer of from 3 to 100.
More preferred is the following structure:

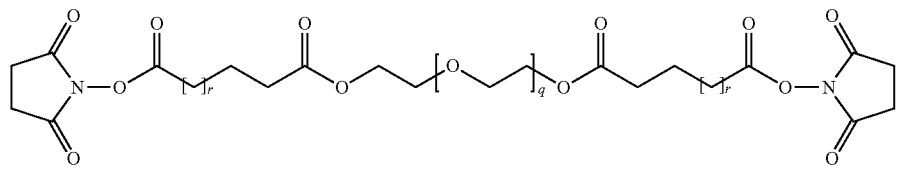

q~45 wherein r is either 1 or 2, preferably 1.

Alternatively, the bis dicarboxylic acid PEG half esters may be activated in the presence of a coupling agent such as DCC or PyBOP.

In an alternative embodiment the backbone reagent carries carboxyl groups and the corresponding crosslinker reagent would be selected from ester-containing amino-terminated PEG-chains.

Backbone reagent and crosslinker reagent may be polymerized to form the hydrogel according to the invention using inverse emulsion polymerization. After selecting the desired stoichiometry between backbone and crosslinker polymerizable groups, backbone and crosslinker are dissolved in DMSO and a suitable emulator with an appropriately selected HLB value, preferably Arlacel P135, is employed to form an inverse emulsion using a mechanical stirrer and controlling the stirring speed. Polymerization is initiated by the addition of a suitable base, preferably by N,N,N',N'-tetramethylethylenene diamine. After stirring for an appropriate amount of time, the reaction is quenched by the addition of an acid, such as acetic acid and water. The beads are harvested, washed, and fractionated according to particle size by mechanical sieving. Optionally, protecting groups may be removed at this stage.

In an alternative embodiment of this invention, multi-functional moieties are coupled to the reactive functional groups of the polymerized reactive hydrogel to increase the number of functional groups which allows increasing the drug load of the hydrogel. Such multi-functional moieties may be provided by suitably substituted derivatives of lysine, dilysine, trilysine, tetralysine, pentalysine, hexylysine, heptalysine, or oligolysine, low molecular weight PEI. Preferably, the multi-functional moiety is lysine.

Further, such hydrogel according to the invention may be functionalized with a spacer carrying the same functional group, for instance, amino groups may be introduced into the hydrogel by coupling a heterobifunctional spacer, such as suitably activated COOH-(EG)$_6$-NH-Fmoc (EG-ethylene glycol), and removing the Fmoc-protecting group.

In one embodiment, a paliperidone compound may be directly reacted with a reactive biodegradable hydrogel to form a covalent transient linkage resulting in a hydrogel prodrug according to the invention. Such transient linkage between drug and biodegradable hydrogel is preferably a carbamate or carbonate or ester.

In another embodiment, a paliperidone compound is first conjugated to a spacer in such a fashion that the linkage between drug compound and spacer is a covalent transient linkage such as a carbamate or carbonate or ester linkage, and is subsequently reacted with the reactive biodegradable hydrogel form a prodrug according to the invention.

In yet another embodiment, a paliperidone compound is first conjugated to a linker in such a fashion that the linkage between drug compound and linker is a covalent transient linkage such as an ester or carbonate or carbamate linkage, and is subsequently reacted with a reactive biodegradable hydrogel to form a prodrug according to the invention.

In another embodiment, a paliperidone compound may be directly reacted with a backbone reagent to form a covalent transient linkage, resulting in a paliperidone-backbone reagent according to the invention. Such transient linkage between drug and backbone reagent is preferably an ester or carbonate and said paliperidone backbone reagent may then be used in the polymerization of a hydrogel, resulting in a carrier linked paliperidone prodrug of the present invention.

In an alternative embodiment, a paliperidone compound may be reacted with a prodrug linker reagent and the resulting paliperidone-linker conjugate is then reacted with a backbone reagent by forming a stable bond between the linker moiety and the backbone moiety. The resulting paliperidone-linker-backbone reagent may then be used in the polymerization of a hydrogel, resulting in a carrier-linked paliperidone prodrug of the present invention.

In another embodiment, a paliperidone compound may be reacted with a prodrug linker reagent and then an activated paliperidone linker conjugate is conjugated to the functional group or groups of a multi-functional moiety. Preferably, the multi-functional moiety is lysine and the stoicheometry is two activated paliperidone-linker conjugates per lysine moiety. This (paliperidone-linker)$_2$-lysine conjugate is activated and then reacted with a backbone reagent by forming a stable bond between the multi-functional moiety and the backbone moiety. The resulting (paliperidone-linker)$_2$-lysine-backbone reagent may then be used in the polymerization of a hydrogel, resulting in a carrier-linked paliperidone prodrug of the present invention.

A particularly preferred method for the preparation of a prodrug of the present invention comprises the steps of (a) reacting a compound of formula $C(A'-X^1)_4$, wherein $A'-X^1$ represents A before its binding to Hyp or a precursor of Hyp and $X^1$ is a suitable chemical functional group, with a compound of formula $Hyp'-X^2$, wherein $Hyp'-X^2$ represents Hyp before its binding to A or a precursor of Hyp and $X^2$ is a suitable chemical functional group to react with $X^1$;

(b) optionally reacting the resulting compound from step (a) in one or more further steps to yield a compound of formula $C(A-Hyp)^4$ having at least four chemical functional groups;

(c) reacting the at least four chemical functional groups of the resulting compound from step (b) with a poly(ethylene glycol) based crosslinker precursor reagent, wherein the crosslinker precursor reagent is used in a sub-stoichiometric amount compared to the total number of functional groups of $C(A-Hyp)^4$ to yield a hydrogel according to the invention;

(d) reacting remaining un-reacted reactive functional groups (representing the reactive functional groups of the backbone comprised in the reactive biodegradable hydrogel of the present invention) in the hydrogel backbone of step (c) with a covalent conjugate of biologically active moiety and transient prodrug linker or first reacting the un-reacted reactive functional groups with the transient prodrug linker and subsequently with the biologically active moiety;

(e) optionally capping remaining un-reacted reactive functional groups to yield a prodrug of the present invention.

Specifically, hydrogels of the present invention are synthesized as follows:

For bulk polymerization, backbone reagent and crosslinker reagent are mixed in a ratio amine groups/active ester groups of 5:1 to 1.05:1, preferably of 4:1 to 1.05:1, more preferably of 3:1 to 1.05:1 and even more preferably of 2:1 to 1.05:1.

Both backbone reagent and crosslinker reagent are dissolved in DMSO to give a solution with a concentration of 5 to 50 g per 100 mL, preferably 7 to 30 g per 100 ml, more preferably 7.5 to 20 g per 100 ml and most preferably 10 to 20 g per 100 ml.

To effect polymerization, 2 to 10% (vol.) N,N,N',N'-tetramethylethylene diamine (TMEDA) are added to the DMSO solution containing crosslinker reagent and backbone reagent and the mixture is shaken for 1 to 20 sec and left standing. The mixture solidifies within less than 1 min.

Such hydrogel according to the invention is preferably comminuted by mechanical processes such as stirring, crushing, cutting pressing, or milling, and optionally sieving.

For emulsion polymerization, the reaction mixture is comprised of the dispersed phase and the continuous phase.

For the dispersed phase, backbone reagent and crosslinker reagent are mixed in a ratio amine/active ester of 5:1 to 1.05:1, preferably of 2:1 to 1.05:1 and are dissolved in DMSO to give a to give a solution with a concentration of 5 to 50 g per 100 mL, preferably 7 to 30 g per 100 ml, more preferably 7.5 to 20 g per 100 ml and most preferably 10 to 20 g per 100 ml.

The continuous phase is any solvent, that is not miscible with DMSO, not basic, aprotic and shows a viscosity lower than 10 Pa*s. Preferably, the solvent is not miscible with DMSO, not basic, aprotic, shows a viscosity lower than 2 Pa*s and is non-toxic. More preferably, the solvent is a saturated linear or branched hydrocarbon with 5 to 10 carbon atoms. Most preferably, the solvent is n-heptane.

To form an emulsion of the dispersed phase in the continuous phase, an emulsifier is added to the continuous phase before adding the dispersed phase. The amount of emulsifier is 2 to 50 mg per ml, dispersed phase, more preferably 5 to 20 mg per mL, dispersed phase, most preferably 10 mg per mL dispersed phase.

The emulsifier has an HLB-value of 3 to 8. Preferably, the emulsifier is a triester of sorbitol and a fatty acid or an poly (hydroxyl fatty acid)-poly(ethylene glycol) conjugate. More preferably, the emulsifier is an poly(hydroxy-fatty acid)-polyethylene glycol conjugate, with a linear poly(ethylene glycol) of a molecular weight in the range of from 0.5 kDa to 5 kDa and poly(hydroxy-fatty acid) units of a molecular weight in the range of from 0.5 kDa to 3 kDa on each end of the chain. Most preferably, the emulsifier is poly(ethylene glycol) dipolyhydroxy stearate, (Cithrol DPHS (Cithrol DPHS, former Arlacel P135, Croda International Plc).

Droplets of the dispersed phase are generated by stirring with an axial flow impeller with a geometry similar to stirrers such as Isojet, Intermig, Propeller (EKATO Rühr- und Mischtechnik GmbH, Germany)), most preferably similar to Isojet or Propeller with a diameter of 50 to 90% of the reactor diameter. Preferably, stirring is initiated before addition of the dispersed phase. Stirrer speed is set to 0.6 to 2.4 m/s, such as 0.8 to 2.3 m/s, preferably to 0.6 to 1.7 m/s. The dispersed phase is added at room temperature, and the concentration of the disperse phase is 2% to 70%, preferably 5 to 50%, more preferably 10 to 40%, and most preferably 20 to 35% of the total reaction volume. The mixture of dispersed phase, emulsifier and continuous phase is stirred for 5 to 60 min before adding the base to the effect polymerization.

5 to 10 equivalents (referred to each amide bond to be formed) of a base are added to the mixture of dispersed and continuous phase. The base is aprotic, non nucleophilic and soluble in the disperse phase. Preferably, the base is aprotic, non nucleophilic, well soluble in both disperse phase and DMSO. More preferably, the base is aprotic, non nucleophilic, well soluble in both disperse phase and DMSO, an amine base and non-toxic. Most preferably, the base is N,N,N',N'-tetramethylethylene diamine (TMEDA). Stirring in the presence of base is continued for 1 to 16 h.

During stirring, droplets of dispersed phase are hardened to become crosslinked hydrogel beads according to the invention which can be collected and fractionation according to size is performed on a vibrational continuous sieving machine with a 75 μm and a 32 μm deck to give hydrogel microparticles according to the invention.

The hydrogel for the prodrug of the present invention can be obtained from the preparation methods in form of microparticles. In a preferred embodiment of the invention, the reactive hydrogel is a shaped article such as a mesh or a stent. Most preferably, the hydrogel is formed into microparticulate beads which can be administered as subcutaneous or intramuscular injectably by means of a standard syringe. Such soft beads may have a diameter of between 1 and 500 micrometer.

Preferably, such beaded paliperidone hydrogel prodrugs have a diameter of between 10 and 100 micrometer if suspended in an isotonic aqueous formulation buffer, most preferably a diameter of between 20 and 100 micrometer, most preferably a diameter of between 25 and 80 micrometer.

Preferably, such beaded biodegradable hydrogel prodrugs can be administered by injection through a needle smaller than 0.6 mm inner diameter, preferably through a needle smaller than 0.3 mm inner diameter, more preferably through a needle small than 0.25 mm inner diameter, even more preferably through a needle smaller than 0.2 mm inner diameter, and most preferably through a needle small than 0.16 mm inner diameter.

It is understood that the terms "can be administered by injection", "injectable" or "injectability" refer to a combination of factors such as a certain force applied to a plunger of a syringe containing the biodegradable hydrogel according to the invention swollen in a liquid at a certain concentration (w/v) and at a certain temperature, a needle of a given inner diameter connected to the outlet of such syringe, and the time required to extrude a certain volume of the biodegradable hydrogel carrier according to the invention from the syringe through the needle.

In order to provide for injectability, a volume of 1 mL of the paliperidone prodrugs according to the invention swollen in water to a concentration of at least 5% (w/v) and contained in a syringe holding a plunger of a diameter of 4.7 mm can be extruded at room temperature within 10 seconds by applying a force of less than 60 Newton, such as less than 50 Newton, preferably by applying a force of less than 40 Newton. Preferably injectability measurement is carried out for an paliperidone prodrug according to the invention swollen in water to a concentration of ca. 15% (w/v).

In a further embodiment the composition of the present invention is used in treating a psychotic disease or disorder in a subject.

In a still further embodiment the composition of the present invention is for use in treatment of a psychotic disease or disorder in a subject, and the term "subject" as used herein, refers to a human, who has been diagnosed with, the object of treatment; or experiment for a "mental disorder" and "mental illness" refer to those provided in the Diagnostic and Statistical Manual (DSM IV), American Psychological Association (APA). Those of ordinary skill in the art will appreciate that formulations of paliperidone compounds can be administered to psychiatric patients for all the known uses of risperidone. These mental disorders include, but are not limited to, schizophrenia; bipolar disorder or other disease states in which psychosis, aggressive behavior, anxiety or depression is evidenced. Schizophrenia refers to conditions characterized as schizophrenia, schizoaffective disorder and schizophreniform disorders, in DSM-IV-TR such as category 295.xx. Bipolar Disorder refers to a condition characterized as a Bipolar Disorder, in DSM-IV-TR such as category 296.xx including Bipolar I and Bipolar Disorder II. The DSM-IV-TR was prepared by the Task Force on Nomenclature and Statistics of the American Psychiatric Association, and provides clear descriptions of diagnostic categories. Pathologic psychological conditions, which are psychoses or may be associated with psychotic features include, but are not limited to the following disorders that have been characterized in the DSMIV-TR. Diagnostic and Statistical Manual of Mental Disorders, Revised, 3rd Ed. (1994). The numbers in parenthesis refer to the DSM-IV-TR categories. The skilled artisan will recognize that there are alternative nomenclatures, nosologies, and classification systems for pathologic psychological conditions and that these systems evolve with medical scientific progress. Examples of pathologic psychological conditions which may be treated include, but are not limited to, Mild Mental Retardation (317), Moderate Mental Retardation (318.0), Severe Mental Retardation (318.1), Profound Mental Retardation (318.2), Mental Retardation Severity Unspecified (319), Autistic Disorders (299.00), Rett's Disorder (299.80), Childhood Disintegrative Disorders (299.10), Asperger's Disorder (299.80), Pervasive Developmental Disorder Not Otherwise Specified (299.80), Attention Deficit/Hyperactivity Disorder Combined Type (314.01), Attention/Deficit Hyperactivity Disorder Predominately Inattentive Type (314.00), Attention-Deficit/Hyperactivity Disorder Predominately Hyperactive-Impulsive Type (314.01), Attention-Deficit/Hyperactivity Disorder NOS (314.9), Conduct Disorder (Childhood Onset and Adolescent Type 312.8), Oppositional Defiant Disorder (313.81), Disruptive Behavior Disorder Not Otherwise Specified (312.9), Solitary Aggressive Type (312.00), Conduct Disorder, Undifferentiated Type (312.90), Tourette's Disorder 15 (307.23), Chronic Motor Or Vocal Tic Disorder (307.22), Transient Tic Disorder (307.21), Tic Disorder NOS (307.20), Alcohol Intoxication Delirium (291.0), Alcohol Withdrawal Delirium (291.0), Alcohol-Induced Persisting Dementia (291.2), Alcohol Induced Psychotic Disorder with Delusions (291.5), Alcohol Induced Psychotic Disorder with Hallucinations (291.3), Amphetamine or Similarly Acting Sympathomimetic Intoxication (292.89), Amphetamine or Similarly Acting Sympathomimetic Delirium (292.81), Amphetamine or Similarly Acting Sympathomimetic Induced Psychotic with Delusions (292.11), Amphetamine or Similarly Acting Sympathomimetic Induced Psychotic with Hallucinations (292.12), Cannabis-Induced Psychotic Disorder with Delusions (292.11), Cannabis-Induced Psychotic Disorder with Hallucinations (292.12), Cocaine Intoxication (292.89), Cocaine Intoxication Delirium (292.81), Cocaine-Induced Psychotic Disorder with Delusions (292.11), Cocaine-Induced Psychotic Disorder with Hallucinations (292.12), Hallucinogen Intoxication (292.89), Hallucinogen Intoxication Delirium (292.81), Hallucinogen-Induced Psychotic disorder with Delusions (292.11), Hallucinogen-Induced Psychotic disorder with Delusions (292.12), Hallucinogen-Induced Mood Disorder (292.84), Hallucinogen:-Induced Anxiety Disorder (292.89), Hallucinogen Related Disorder Not Otherwise Specified (292.9), Inhalant Intoxication (292.89), Inhalant Intoxication Delirium (292.81), Inhalant Induced Persisting Dementia (292.82), Inhalant-Induced Psychotic Disorder with Delusions (292.11), Inhalant Induced Psychotic with Hallucinations (292.12), Inhalant Induced Mood Disorder (292.89), Inhalant Induced Anxiety Disorder (292.89), Inhalant Related Disorder Not Otherwise Specified (292.9), Opioid Intoxication Delirium (292.81), Opioid-Induced Psychotic Disorder with Delusions (292.11), Opioid intoxication Delirium (292.81), Opioid-Induced Psychotic Disorder with Hallucinations (292.12), Opioid-Induced Mood Disorder (292.84), Phencyclidine (PCP) or Similarly Acting Arylcyclohexylamine Intoxication (292.89), Phencyclidine (PCP) or Similarly Acting Arylcyclohexylamine Intoxication Delirium (292.81), Phencyclidine (PCP) or Similarly Acting Arylcyclohexylamine Induced Psychotic Disorder with Delusions (292.11), Phencyclidine (PCP) or Similarly Acting Arylcyclohexylamine Induced Psychotic Disorder with Hallucinations (292.12), Phencyclidine (PCP) or Similarly Acting Arylcyclohexylamine Mood Disorder (292.84), Phencyclidine (PCP) or Similarly Acting Arylcyclohexylamine Induced Anxiety Disorder (292.89), Phencyclidine (PCP) or Similarly Acting Arylcyclohexylamine Related Disorder Not Otherwise Specified (292.9), Sedative, Hypnotic or Anxiolytic Intoxication (292.89), Sedation, Hypnotic or Anxiolytic Intoxication Delirium (292.81), Sedation, Hypnotic or Anxiolytic Withdrawal Delirium (292.81), Sedation, Hypnotic or Anxiolytic Induced Persisting Dementia (292.82), Sedation, Hypnotic or Anxiolytic-Induced Psychotic Disorder with Delusions (292.11), Sedation, Hypnotic or Anxiolytic-Induced Psychotic Disorder with Hallucinations (292.12), Sedation, Hypnotic or Anxiolytic-Induced Mood Disorder (292.84), Sedation, Hypnotic or Anxiolytic-Induced Anxiety Disorder (292.89), Other (or Unknown) Substance Intoxication (292.89), Other (or Unknown) Substance Induced Delirium (292.81), Other (or Unknown) Substance-Induced Persisting Dementia (292.82), Other (or Unknown) Substance-Induced Psychotic Disorder with Delusions (292.11), Other (or Unknown) Substance-Induced Psychotic Disorder with Hallucinations (292.12), Other (or Unknown) Substance-Induced Mood Disorder (292.81), Other (or Unknown) Substance-Induced Anxiety Disorder (292.89), Other (or Unknown) Substance Disorder Not Otherwise Specified (292.9), Obsessive Compulsive Disorder (300.3), Post-traumatic Stress Disorder (309.81), Generalized Anxiety Disorder (300.02), Anxiety Disorder Not Otherwise Specified (300.00), Body Dysmorphic Disorder (300.7), Hypochondriasis (or Hypochondriacal Neurosis) (300.7), Somatization Disorder (300.81), Undifferentiated Somatoform Disorder (300.81), Somatoform Disorder Not Otherwise Specified (300.81), Intermittent Explosive Disorder (312.34), Kleptomania (312.32), Pathological Gambling (312.31), Pyromania (312.33), Trichotillomania (312.39), and Impulse Control Disorder NOS (312.30), Schizophrenia, Paranoid Type, (295.30), Schizophrenia, Disorganized (295.10), Schizophrenia, Catatonic Type, (295.20), Schizophrenia, Undifferentiated Type (295.90), Schizophrenia, Residual Type (295.60), Schizophreniform Disorder (295.40), Schizoaffective Disorder (295.70), Delusional Disorder (297.1), Brief Psychotic Disorder (298.8), Shared Psychotic Disorder (297.3), Psychotic Disorder Due to a General Medical Condition with Delusions (293.81), Psychotic Disorder Due to a General Medical Condition with Hallucinations (293.82), Psychotic Disorders Not 15 Otherwise Specified (298.9), Major Depression, Single Episode, Severe, without Psychotic Features (296.23), Major Depression, Recurrent, Severe, without Psychotic Features (296.33), Bipolar Disorder, Mixed, Severe, without Psychotic Features (296.63), Bipolar Disorder, Mixed, Severe, with Psychotic Features (296.64), Bipolar Disorder, Manic, Severe, without Psychotic Features (296.43), Bipolar Disorder, Manic, Severe, with Psychotic Features (296.44), Bipolar Disorder, Depressed, Severe, without Psychotic Features (296.53), Bipolar Disorder, Depressed, Severe, with Psychotic Features (296.54), Bipolar II Disorder (296.89), Bipolar Disorder Not Otherwise Specified (296.80), Personality Disorders, Paranoid (301.0), Personality Disorders, Schizoid (301.20), Personality Disorders, Schizotypal (301.22), Personality Disorders, Antisocial (301.7), and Personality Disorders, Borderline (301.83). All of the above indication can be selected out in individual embodiments and can be used in any combination of aspects and embodiments herein.

Some subjects, such as human subjects, have a history of post-injection delirium or sedation syndrome in connection with being treated for any one of the above indications.

Accordingly, in a further embodiment the composition of the present invention is for use in treating a psychotic disease or disorder in a subject, wherein the subject previously has experienced post-injection delirium/sedation syndrome.

Moreover, in a further embodiment the composition of the present invention is for use in treatment of delusional psychosis, psychotic depression, obsessive-compulsion disorder, schizophrenia, such as acute and maintenance treatment of schizophrenia, preventing recurrence of the symptoms of schizophrenia, bipolar disorder, Asperger's syndrome, and Tourette's syndrome, autistic spectrum disorders, or any combination thereof or any indications mentioned above wherein the subject previously has experienced post-injection delirium/sedation syndrome.

In a still further embodiment the composition of the present invention is for use in preventing post-injection delirium/sedation syndrome in a subject diagnosed with a psychotic disease or disorder.

In a further embodiment the composition of the present invention is for use in preventing post-injection delirium/sedation syndrome in a subject diagnosed with delusional psychosis, psychotic depression, obsessive-compulsion disorder, schizophrenia, such as acute and maintenance treatment of schizophrenia, preventing recurrence of the symptoms of schizophrenia, bipolar disorder, Asperger's syndrome, and Tourette's syndrome, autistic spectrum disorders, or any combination thereof, or any indications mentioned above.

The volume to be administered in order to administer an effective dose, for example by a syringe, to a subject, such as a human, is preferably a volume of not more than 3.0 mL, such as from about 0.20 mL to about 2.0 mL.

In a further embodiment the composition of the present invention is contained in a syringe.

When administered by subcutaneous injection it is preferred that the composition of the present invention does not change physical state before, during and immediately after administration. For instance the injection of beads of a small diameter, such as a mean diameter from 1000 μm to 1 μm, or from 300 μm to 10 μm will fulfill this purpose and avoid side effects.

In a further aspect the present invention relates to use of a paliperidone compound for preparing a pharmaceutical composition for subcutaneous injection wherein the composition releases the paliperidone with an immediate onset of action and continuously for at least 3 weeks, and wherein the composition has a pharmacokinetic profile in vivo with substantially no burst release of paliperidone for treatment of a psychotic disease or disorder in a subject.

In a further aspect the present invention relates to use of a paliperidone compound for preparing a pharmaceutical composition for subcutaneous injection wherein the composition releases the paliperidone with an immediate onset of action and continuously for at least 3 weeks, and wherein the composition has a pharmacokinetic profile in vivo with substantially no burst release of paliperidone for treatment of delusional psychosis, psychotic depression, obsessive-compulsion disorder, schizophrenia, such as acute and maintenance treatment of schizophrenia, preventing recurrence of the symptoms of schizophrenia, bipolar disorder, Asperger's syndrome, and Tourette's syndrome, autistic spectrum disorders, or any combination thereof, or any of the indications mentioned above, in a subject.

In a further aspect the present invention relates to use of a paliperidone compound for preparing a pharmaceutical composition for subcutaneous injection wherein the composition comprises the paliperidone compound of a concentration of at least 10 mg/ml based on quantitative release of free paliperidone, which composition releases the paliperidone continuously for at least 3 weeks for treatment of a psychotic disease or disorder in a subject.

In a further aspect the present invention relates to use of a paliperidone compound for preparing a pharmaceutical composition for subcutaneous injection wherein the composition comprises the paliperidone compound of a concentration of at least 10 mg/ml based on quantitative release of free paliperidone, which composition releases the paliperidone continuously for at least 3 weeks for treatment of delusional psychosis, psychotic depression, obsessive compulsion disorder, schizophrenia, such as acute and maintenance treatment of schizophrenia, preventing recurrence of the symptoms of schizophrenia, bipolar disorder, Asperger's syndrome, and Tourette's syndrome, autistic spectrum disorders, or any combination thereof, or any of the indications mentioned above, in a subject.

In an embodiment the composition is characterized by releasing the paliperidone in such way that the therapeutic plasma levels are reached within 24 hours of administration, such as within 18 hours of administration, e.g. within 12 hours of administration.

In a further embodiment the pharmaceutical composition is characterized by having a pharmacokinetic profile in vivo with no burst release of paliperidone.

In a still further embodiment of the pharmaceutical composition the dosage of the paliperidone compound is at least 10 mg, based on quantitative release of free paliperidone from the compound.

In a further embodiment of the pharmaceutical composition the concentration of the paliperidone compound is at least 10 mg/ml, based on quantitative release of free paliperidone from the compound.

In a still further embodiment the composition is characterized by exhibiting a peak to trough ratio of less than 10, such as less than 5, less than 3, or less than 12, preferentially, exhibiting a peak-to-trough ratio at steady state of less than 5, such as less than 4, such as less than 3, or less than 2.

In a further embodiment the pharmaceutical composition is characterized by a continuous release of the paliperidone or compound over the full time period between administrations. Typically, the full time period between administrations (subcutaneous injections) is at least about 3 weeks, such as at least about 4 weeks, e.g. at least 5 weeks. Sometimes it may be preferred to have a continuous release of the paliperidone compound over 6 weeks or more, such as 7 weeks or 8 weeks.

In a still further embodiment the paliperidone compound is a prodrug.

In a further embodiment paliperidone or the paliperidone compound is released from a depot.

In an embodiment paliperidone or the paliperidone compound is fully contained in a depot, typically a polymer gel, such as a hydrogel, e.g. a well hydrated polymer matrix or a biocompatible container.

In another embodiment paliperidone or the paliperidone compound is covalently linked in the depot, typically the polymer gel, such as the hydrogel, e.g. the well hydrated polymer matrix.

In a further embodiment the paliperidone compound is formulated as particles, typically beads, such as particles or beads having a mean diameter of from 1000 µm to 1 µm, such as 300 to 10 µm.

Compositions of paliperidone hydrogel prodrugs are described in the following paragraphs.

The composition of paliperidone hydrogel prodrug may be provided as a suspension composition or as a dry composition. Preferably, the pharmaceutical composition of paliperidone hydrogel prodrug is a dry composition. Suitable methods of drying are, for example, spray-drying and lyophilization (freeze-drying). Preferably, the pharmaceutical composition of paliperidone hydrogel prodrug is dried by lyophilization.

Preferably, the paliperidone hydrogel prodrug is sufficiently dosed in the composition to provide a therapeutically effective amount of paliperidone for at least three days in one application. More preferably, one application of the paliperidone hydrogel prodrug is sufficient for at least one week, such as for one week, two weeks, three weeks, four weeks, five weeks, six weeks, seven weeks, eight weeks, three months, four months, five months or six months.

The pharmaceutical composition of paliperidone hydrogel prodrug according to the present invention contains one or more excipients.

Excipients used in parenteral compositions may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The compositions of paliperidone hydrogel prodrugs according to the present invention contain one or more than one excipient, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability (ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for (iii) Preservatives and/or antimicrobials: multidose parenteral preparations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosal, sorbic acid, potassium sorbate, benzoic acid, chlorocresol, and benzalkonium chloride (iv) Stabilizers: Stabilisation is achieved by strengthening of the protein-stabilising forces, by destabilisation of the denatured starter, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used (v) Anti-adsorption agents: Mainly ionic or non-ionic surfactants or other proteins or soluble polymers are used to coat or adsorb competitively to the inner surface of the composition's or composition's container. Suitable surfactants are e.g., alkyl sulfates, such as ammonium lauryl sulfate and sodium lauryl sulfate; alkyl ether sulfates, such as sodium laureth sulfate and sodium myreth sulfate; sulfonates such as dioctyl sodium sulfosuccinates, perfluorooctanesulfonates, perfluorobutanesulfonates, alkyl benzene sulfonates; phosphates, such as alkyl aryl ether phosphates and alkyl ether phosphates; carboxylates, such as fatty acid salts (soaps) or sodium stearate, sodium lauroyl sarcosinate, perfluorononanoate, perfluorooctanoate; octenidine dihydrochloride; quaternary ammonium cations such as cetyl trimethylammonium bromide, cetyl trimethylammonium chloride, cetylpyridinium chloride, polyethoxylated tallow amine, benzalkonium chloride, benzethonium chloride, 5-bromo-5 nitor-1,3-dioxane, dimethyldioctadecylammonium chloride, dioctadecyldimethylammonium bromide; zwitterionics, such as 3-[(3-cholamidopropyl) dimethylammonio]-1 propanesulfonate, cocamidopropyl hydroxysultaine, amino acids, imino acids, cocamidopropyl betaine, lecithin; fatty alcohols, such as cetyl alcohol, stearyl alcohol, cetostearyl alcohol, oleyl alcohol; polyoxyethylene glycol alkyl ethers, such as octaethylene glycol monododecyl ether, pentaethylene glycol monododecyl ether; polyoxypropylene glycol alkyl ethers; glucoside alkyl ethers, such as decyl glucoside, lauryl glucoside, octyl glucoside; polyoxyethylene glycol octylphenol ethers such as Triton X-100; polyoxyethylene glycol alkylphenol ethers such as nonoxynol-9; glycerol alkyl esters such as glyceryl laurate; polyoxyethylene glycol sorbitan alkyl esters such as polysorbates; sorbitan alkyl esters; cocamide MEA and cocamide DEA; dodecyl dimethylamine oxide; block copolymers of polyethylene glycol and polypropylene glycol, such as poloxamers (Pluronic F-68), PEG dodecyl ether (Brij 35), polysorbate 20 and 80; other anti-absorption agents are dextran, polyethylene glycol, PEG-polyhistidine, BSA and HSA and gelatines. Chosen concentration and type of excipient depends on the effect to be avoided but typically a monolayer of surfactant is formed at the interface just above the CMC value (vi) Lyo- and/or cryoprotectants: During freeze- or spray drying, excipients may counteract the destabilising effects caused by hydrogen bond breaking and water removal. For this purpose sugars and polyols may be used but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used (vii) Oxidation protection agents: antioxidants such as ascorbic acid, ectoine, ethionine, glutathione, monothioglycerol, morin, polyethylenimine (PEI), propyl gallate, vitamin E, chelating agents such aus citric acid, EDTA, hexaphosphate, thioglycolic acid (viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carborner viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly(acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A blocks, such as polylactide (PLA) or poly(lactide-co-glycolide) (PLGA), and hydrophilic B blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(ix) Spreading or diffusing agent: modifies the permeability of connective tissue through the hydrolysis of components of the extracellular matrix in the interstitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture Preferably, the composition of paliperidone hydrogel prodrug contains one or more than one viscosifier and/or viscosity modifying agent.

The term "excipient" preferably refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained release formulations and the like. The composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the therapeutic, preferably in purified form, together with a suitable amount of excipient so as to provide the form for proper administration to the patient. The formulation should suit the mode of administration.

In a general embodiment a pharmaceutical composition of the present invention whether in dry form or as a suspension or in another form may be provided as single or multiple dose composition.

In one embodiment of the present invention, the dry composition of paliperidone hydrogel prodrug is provided as a single dose, meaning that the container in which it is supplied contains one pharmaceutical dose.

In another aspect of the present invention the composition is provided as a single dose composition.

Alternatively, the suspension composition or dried composition is a multiple dose composition, meaning that it contains more than one therapeutic dose. Preferably, a multiple dose composition contains at least 2 doses. Such multiple dose composition of paliperidone hydrogel can either be used for different patients in need thereof or is intended for use in one patient, wherein the remaining doses are stored after the application of the first dose until needed.

In another aspect of the present invention the composition is comprised in a container. Preferably the container is a dual-chamber syringe. Especially the dry composition according to the present invention is provided in a first chamber of the dual-chamber syringe and reconstitution solution is provided in a second chamber of the dual chamber syringe.

Prior to applying the dry composition of paliperidone hydrogel prodrug to a patient in need thereof, the dry composition is reconstituted. Reconstitution can take place in the container in which the dry composition of paliperidone hydrogel prodrug is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials, such as, for example, benzylalcohol and cresol. Preferably, the reconstitution solution is sterile water.

An additional aspect of the present invention relates to the method of administration of a reconstituted paliperidone hydrogel prodrug composition. The paliperidone hydrogel prodrug composition can be administered by methods of injection or infusion, including intradermal, subcutaneous, intramuscular, intravenous, intraosseous, and intraperitoneal. Preferably, the paliperidone hydrogel prodrug is administered subcutaneously.

A further aspect is a method of preparing a reconstituted composition comprising a therapeutically effective amount of a paliperidone hydrogel prodrug, and optionally one or more pharmaceutically acceptable excipients, wherein the paliperidone is transiently linked to a hydrogel, the method comprising the step of
 contacting the composition of the present invention with a reconstitution solution.

Another aspect is a reconstituted composition comprising a therapeutically effective amount of a paliperidone hydrogel prodrug, and optionally one or more pharmaceutically acceptable excipients, wherein the paliperidone is transiently linked to a hydrogel obtainable by the method above.

Another aspect of the present invention is the method of manufacturing a dry composition of paliperidone hydrogel prodrug. In one embodiment, such suspension composition is made by
 (i) admixing the paliperidone hydrogel prodrug with one or more excipients,
 (ii) transferring amounts equivalent to single or multiple doses into a suitable container,
 (iii) drying the composition in said container, and
 (iv) sealing the container.

Suitable containers are vials, syringes, dual-chamber syringes, ampoules, and cartridges.

Another aspect is a kit of parts. When the administration device is simply a hypodermic syringe then the kit may comprise the syringe, a needle and a container comprising the dry paliperidone hydrogel prodrug composition for use with the syringe and a second container comprising the reconstitution solution. In more preferred embodiments, the injection device is other than a simple hypodermic syringe and so the separate container with reconstituted paliperidone hydrogel prodrug is adapted to engage with the injection device such that in use the liquid composition in the container is in fluid connection with the outlet of the injection device. Examples of administration devices include but are not limited to hypodermic syringes and pen injector devices. Particularly preferred injection devices are the pen injectors in which case the container is a cartridge, preferably a disposable cartridge. Optionally, the kit of parts comprises a safety device for the needle which can be used to cap or cover the needle after use to prevent injury.

A preferred kit of parts comprises a needle and a container containing the composition according to the present invention and optionally further containing a reconstitution solution, the container being adapted for use with the needle. Preferably, the container is a dual-chamber syringe.

In another aspect, the invention provides a cartridge containing a composition of paliperidone hydrogel prodrug as hereinbefore described for use with a pen injector device. The cartridge may contain a single dose or multiplicity of doses of paliperidone.

In a further embodiment the composition of the present invention is for use in treating a psychotic disease or disorder in a subject, wherein the subject previously has experienced post-injection delirium/sedation syndrome.

In a still further embodiment the composition of the present invention is for use in treatment of delusional psychosis, psychotic depression, obsessive-compulsion disorder, schizophrenia, such as acute and maintenance treatment of schizophrenia, preventing recurrence of the symptoms of schizophrenia, bipolar disorder, Asperger's syndrome, and Tourette's syndrome, autistic spectrum disorders, or any combination thereof, or any of the above mentioned indications, wherein the subject previously has experienced post-injection delirium/sedation syndrome.

In a further embodiment the composition of the present invention is for use in preventing post-injection delirium/sedation syndrome in a subject diagnozed with a psychotic disease or disorder.

In a still further embodiment the composition of the present invention is for use in preventing post-injection delirium/sedation syndrome in a subject diagnozed with delusional psychosis, psychotic depression, obsessive-compulsion disorder, schizophrenia, such as acute and maintenance treatment of schizophrenia, preventing recurrence of the symptoms of schizophrenia, bipolar disorder, Asperger's syndrome, and Tourette's syndrome, autistic spectrum disorders, or any combination thereof, or any of the above mentioned indications.

The volume to be administered in order to administer an effective dose, for example by a syringe, to a subject, such as a human, is preferably a volume of not more than 3.0 mL, such as from about 0.20 mL to about 2.0 mL.

In a further embodiment the composition of the present invention is contained in a syringe.

When administered by subcutaneous injection it is preferred that the composition of the present invention does not change physical state before, during and immediately after administration. Such composition may be particles, e.g. beads.

In a further aspect the present invention relates to a method of treating a psychotic disease or disorder, or delusional psychosis, psychotic depression, obsessive-compulsion disorder, schizophrenia, such as acute and maintenance treatment of schizophrenia, preventing recurrence of the symptoms of schizophrenia, bipolar disorder, Asperger's syndrome, and Tourette's syndrome, autistic spectrum disorders, or any combination thereof, in a subject, in need of such a treatment or prevention by administration of a therapeutically effective amount of a pharmaceutical composition of any one of the above aspects or embodiments as well as any combination thereof as described herein.

In a further aspect the present invention relates to a kit of parts comprising a pharmaceutical composition of any one of the above aspects or embodiments as well as any combination thereof as described herein and a container for administration of the composition. Typically, the container is a syringe.

It is to be understood that whenever an aspect herein referrers to other aspects or embodiments such referral should be given broadest interpretation unless otherwise stated, for instance, if a first aspect or embodiment is later limited for whatever reason, then a second aspect referring to said first aspect or embodiment should be considered to hold the original broadest meaning of the first aspect or embodiment before the limitation.

EXAMPLES

Materials and Methods

Paliperidone was purchased from Carbon Scientific Co., Ltd, London, U.K. Fmoc Ado-OH and boc-3-amino-2,2-dimethyl-propionic acid were purchased from Polypeptide group, Strasbourg, France. Adipic anhydride was purchased from Wako Chemicals GmbH, Neuss, Germany. Amino 4-arm PEG5000 was obtained from JenKem Technology, Beijing, P. P. China. Amino 4-arm PEG2000 was obtained from CreativePEGWorks, Winston Salem, N.C., USA.

All other chemicals were purchased from Sigma-ALDRICH Chemie GmbH, Taufkirchen, Germany.

RP-HPLC Purification:

RP-HPLC was done on a 100×20 or a 100×40 mm C18 ReproSil-Pur 300 ODS-3 5μ column (Dr. Maisch, Ammerbuch, Germany) connected to a Waters 600 HPLC System and Waters 2487 Absorbance detector. Linear gradients of solution A (0.1% TFA in $H_2O$) and solution B (0.1% TFA in acetonitrile or 0.1% TFA in 2/1 (v/v) methanol/isopropanol) were used. HPLC fractions containing product were lyophilized. Alternatively, if the HCl salt of the purified product was desired, TFA was replaced by 0.01% HCl (v/v, 37% HCl) in solution A and solution B.

Analytics: Ultra performance liquid chromatography-electrospray ionization mass spectrometry (UPLC-ESI-MS) was performed on a Waters Acquity Ultra Performance LC instrument connected to a Thermo scientific LTQ Orbitrap Discovery instrument and spectra were, if necessary, interpreted by Thermo scientific software xcalibur. M/z signals corresponding to the most abundant isotope are given.

Mass spectra of polydisperse PEG products showed a series of $(CH_2CH_2O)_n$ moieties due to polydispersity of PEG starting materials. For easier interpretation only one single representative m/z signal is given in the examples.

The quantification of plasma paliperidone concentrations were carried out using a Waters Acquity UPLC coupled to a Thermo LTQ Orbitrap Discovery mass spectrometer via an ESI probe and with Waters BEH C18 (50×2.1 mm I.D., 1.7 μm particle size) as analytical column (mobile phase A: 10 mM ammonium formate pH 4.0, mobile phase B: acetonitrile, T=45° C.). The gradient system comprised a linear gradient from 10% B to 50% B in 4 min, an isocratic washing phase with 95% B (1.5 min), and a reconditioning phase (2.5 min) with a flow rate of 0.25 mL/min. Detection of the ions was performed in the selected reaction monitoring (SRM) mode, monitoring the transition pairs at the m/z 427.2 precursor ions to the m/z 207.1 product ion ions for paliperidone and m/z 376.1 precursor ions to the m/z 165.1 product ions for the internal standard (IS) haloperidol.

After addition of aq. NaOH (50 μL, 0.5 M NaOH) the thawed plasma samples (~95 μL) were spiked with 220 pg haloperidol (10 μl of an aqueous haloperidol solution c=22 pg/μL) and extracted with diethyl ether (2×500 μL). The aqueous layer was frozen in a liquid nitrogen bath and the organic layer was transferred to a separate tube. The solvent of the combined organic phase was removed in a stream of nitrogen at 40° C. and the residue was dried in vacuo. The residues at different time points were dissolved in mobile phase A:mobile phase B=7:3 (v/v) (100 μL) and aliquots (15 μL) were injected into the HPLC-MS system.

The calibration curve was acquired by plotting the peak area of paliperidone against the nominal amount of calibration standards. The results were fitted to linear regression using standard software.

The paliperidone peak areas of the quantification experiments at different time points were weighted relatively to the ratio (mean peak area IS of all experiments)/(peak area IS). The resulting peak areas were used to calculate the paliperidone concentration in plasma (ng $mL^{-1}$).

Analysis Hydrogel Degradation:

Hydrogel degradation was analysed by monitoring release of water soluble (backbone moieties containing) macromonomers from hydrogel by SEC. Paliperidone-linker-hydrogel samples containing approximately 0.85 mg paliperidone were washed three times with pH 7.4 phosphate buffer (60 nM, 3 mM EDTA, 0.01% Tween-20) and filled-up to 1.5 mL using the same buffer. Samples were incubated at 37° C. and aliquots of supernatant were analyzed at various time points by means of SEC (Superdex75 5/150 GL column, GE Healthcare, eluent: 20 mM phosphate buffer pH 7.4, 150 mM NaCl, 0.005% Tween 20+acetonitrile (9/1, v/v), flow: 0.35 ml/min). Signals of macromonomers at 0.9-1.7 min were integrated (215 nm) and plotted versus time.

Example 1

Synthesis of Paliperidone Dicarboxylic Acid Hemiesters

General Procedure for Synthesis of Paliperidone-Esters:

Paliperidone (1 eq) was dissolved in DCM (dry, mol. sieve) and triethylamine (4.4 eq), a catalytic amount of DMAP and the suitable cyclic anhydride (4 eq) were successively added. The reaction mixture was then allowed to stir for 1-24 h at RT. Volatiles were removed and the resulting mixture was diluted with ACN/water 1/1+0.1% TFA and acidified with acetic acid until pH reached about 4. The respective product was purified by RP-HPLC and HPLC fractions containing product were pooled and lyophilized.

Synthesis of Intermediate (1a):

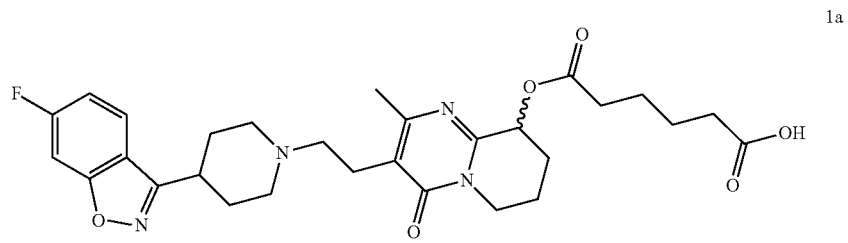 [SMILES: Cc1nc2n(c(=O)c1CCN1CCC(c3noc4cc(F)ccc34)CC1)CCCC2OC(=O)CCCCC(=O)O]

1a was synthesized as described according to the general procedure for the synthesis of paliperidone-esters from 1.50 g of paliperidone and adipic anhydride to afford a white solid.

Yield: 1.45 g (2.45 mmol, 70%, HCl salt).
MS: m/z 555.3=[M+H]$^+$. (MW calculated=554.6)

Synthesis of Intermediate (1b):

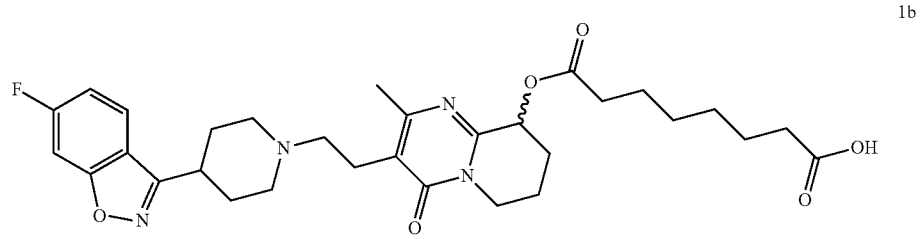 [SMILES: Cc1nc2n(c(=O)c1CCN1CCC(c3noc4cc(F)ccc34)CC1)CCCC2OC(=O)CCCCCCC(=O)O]

1b was synthesized from 130 mg of paliperidone and suberic anhydride according to the general procedure for the synthesis of paliperidone-esters, leading to a white solid.

Yield: 93 mg (0.133 mmol, 43%, TFA salt).
MS: m/z 583.3=[M+H]$^+$ (MW calculated=582.7)

Synthesis of Intermediate (1c):

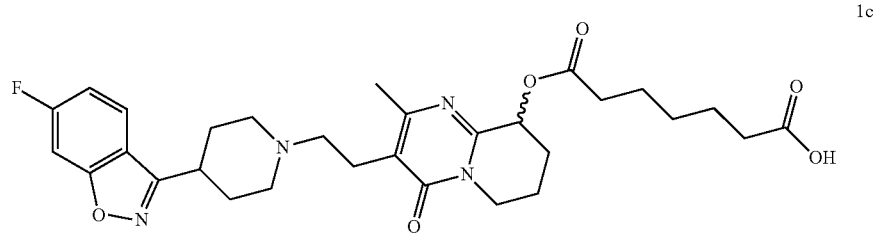 [SMILES: Cc1nc2n(c(=O)c1CCN1CCC(c3noc4cc(F)ccc34)CC1)CCCC2OC(=O)CCCCCC(=O)O]

1c was synthesized from 500 mg of paliperidone and pimelic anhydride according to the general procedure for the synthesis of paliperidone-esters to yield a white solid.

Yield: 483 mg (0.799 mmol, 68%, HCl salt).
MS: m/z 569.3=[M+H]$^+$ (MW calculated=568.7)

Synthesis of Intermediate (1d):

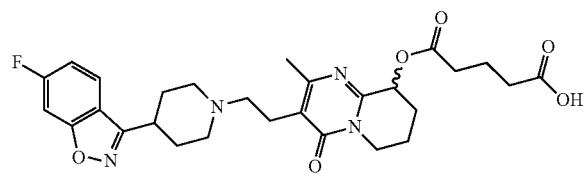

1d was synthesized from 650 mg of paliperidone and glutaric anhydride according to the general procedure for the synthesis of paliperidone-esters, leading to a white solid.

Yield: 700 mg (1.21 mmol, 80%, HCl salt).
MS: m/z 541.2=[M+H]$^+$ (MW calculated=540.7)

Alternatively 1d was synthesized by adding 5.35 g glutaric anhydride and 2.84 mL pyridine to a solution of 2.00 g paliperidone in 30 mL DCM (dry, mol. sieve). The reaction mixture was then allowed to stir for 3 d at RT. Volatiles were removed and the resulting mixture was diluted with ACN/water 1/1+0.1% TFA and acidified with acetic acid until pH reached about 4. 1d was purified by RP-HPLC and HPLC fractions containing product were pooled and lyophilized, leading to a white solid.

Yield: 1.60 g (2.77 mmol, 60%, HCl salt).
MS: m/z 541.2=[M+H]$^+$ (MW calculated=540.7)

Synthesis of Intermediate (1e):

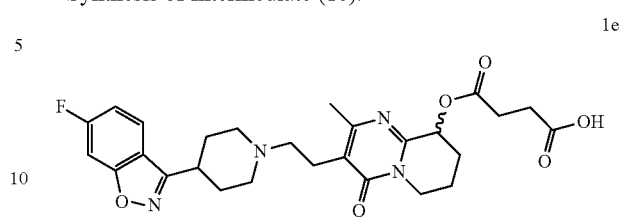

1e was synthesized from 513 mg of paliperidone and succinic anhydride according to the general procedure for the synthesis of paliperidone-esters, leading to a white solid.

Yield: 555 mg (0.99 mmol, 82%, HCl salt).
MS: m/z 527.2=[M+H]$^+$ (MW calculated=526.6)

Example 2

Synthesis of Backbone Reagents (2g) and (2h)

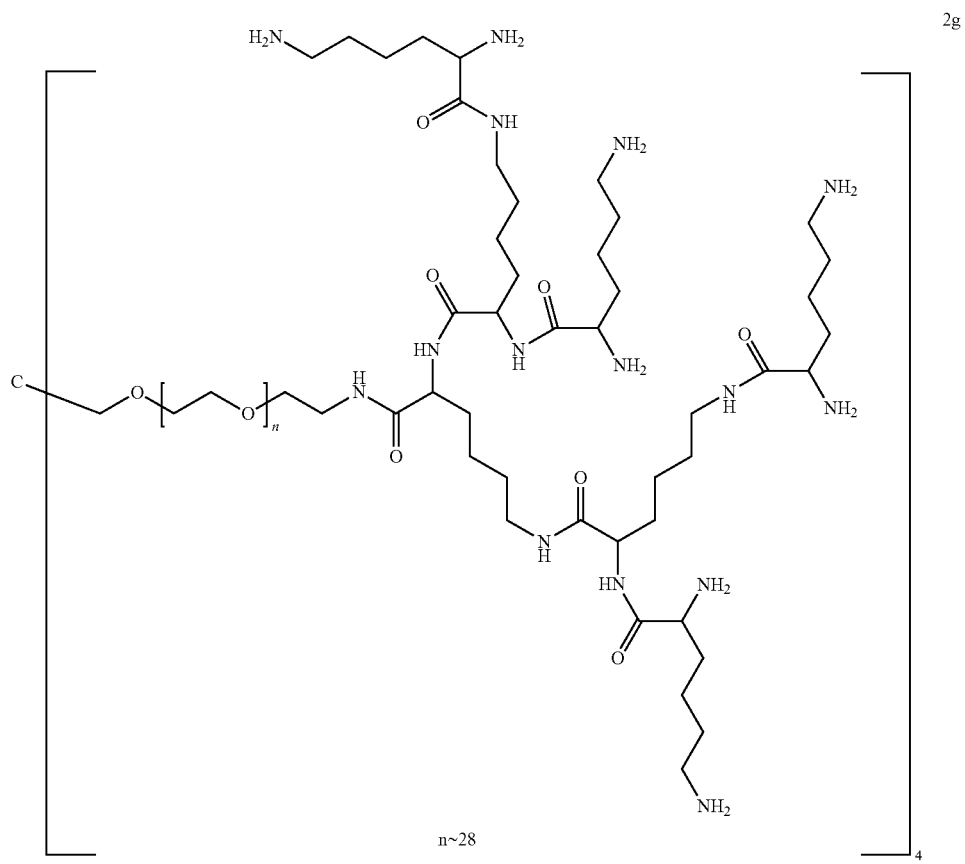

Backbone reagent 2g was synthesized from Amino 4-arm PEG5000 2a according to following scheme:

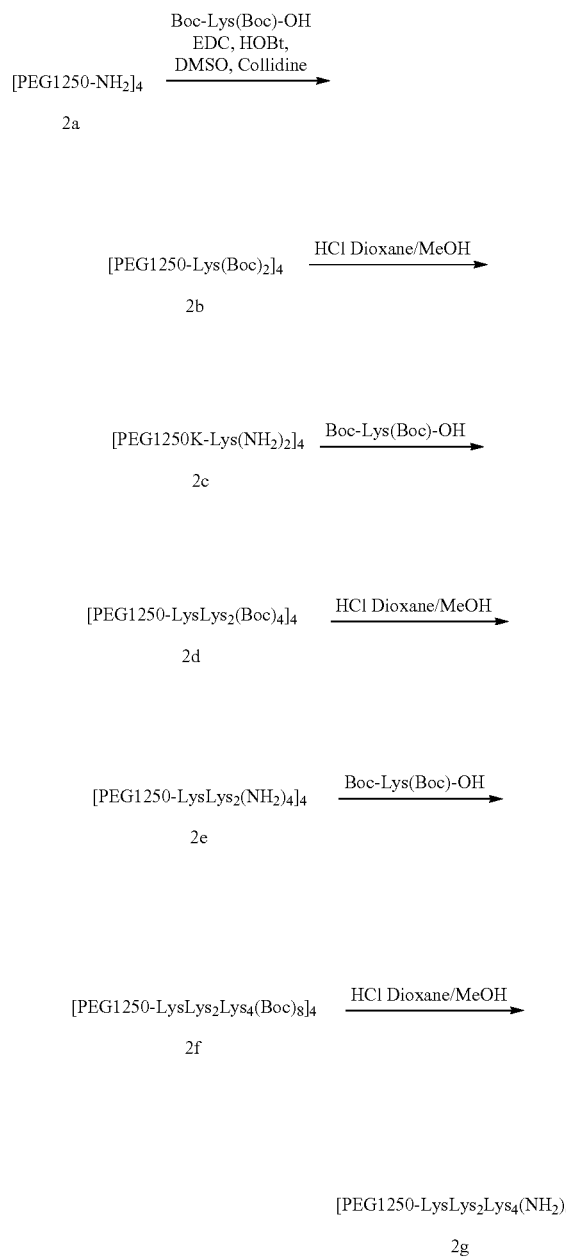

For synthesis of compound 2b, 4-Arm-PEG5000 tetraamine 2a (MW ca. 5200 g/mol, 5.20 g, 1.00 mmol, HCl salt) was dissolved in 20 mL of DMSO (anhydrous). Boc-Lys(Boc)-OH (2.17 g, 6.25 mmol) in 5 mL of DMSO (anhydrous), EDC HCl (1.15 g, 6.00 mmol), HOBt. H$_2$O (0.96 g, 6.25 mmol), and collidine (5.20) mL, 10 mmol) were added. The reaction mixture was stirred for 30 min at RT.

The reaction mixture was diluted with 1200 mL of dichloromethane and washed with 600 mL, of 0.1 N H$_2$SO$_4$ (2×), brine (1×), 0.1 M NaOH (2×), and 1/1 (v/v) brine/water (4×). Aqueous layers were reextracted with 500 mL of DCM. Organic phases were dried over Na$_2$SO$_4$, filtered and evaporated to give 6.3 g of crude product 2b as colorless oil. Compound 2b was purified by RP-HPLC.

Yield 3.85 g (59%) colorless glassy product 2b.

MS: m/z 1294.4=[M+5H]$^{5+}$ (MW calculated=1294.6).

Compound 2c was obtained by stirring of 3.40 g of compound 2b (0.521 mmol) in 5 mL of methanol and 9 mL of 4 N HCl in dioxane at RT for 15 min. Volatiles were removed in vacuo. The product was used in the next step without further purification.

MS: m/z 1151.9=[M+5H]$^{5+}$ (MW calculated=1152.0).

For synthesis of compound 2d, 3.26 g of compound 2c (0.54 mmol) were dissolved in 15 mL of DMSO (anhydrous), 2.99 g Boc-Lys(Boc)-OH (8.64 mmol) in 15 mL DMSO (anhydrous), 1.55 g EDC HCl (8.1 mmol), 1.24 g HOBt.H$_2$O (8.1 mmol), and 5.62 mL of collidine (43 mmol) were added. The reaction mixture was stirred for 30 min at RT.

Reaction mixture was diluted with 800 mL DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried with Na$_2$SO$_4$, filtered and evaporated to give a glassy crude product.

Product was dissolved in DCM and precipitated with cooled (−18° C.) diethylether. This procedure was repeated twice and the precipitate was dried in vacuo.

Yield: 4.01 g (89%) colorless glassy product 2d, which was used in the next step without further purification.

MS: m/z 1405.4=[M+6H]$^{6+}$ (MW calculated=1405.4).

Compound 2e was obtained by stirring a solution of compound 2d (3.96 g, 0.17 mmol) in 7 mL of methanol and 20 mL of 4 N HCl in dioxane at RT for 15 min. Volatiles were removed in vacuo. The product was used in the next step without further purification.

MS: m/z 969.6=[M+7H]$^{7+}$ (MW calculated=969.7).

For the synthesis of compound 2f, compound 2e (3.55 g, (0.48 mmol) was dissolved in 20 mL of DMSO (anhydrous). Boc-Lys(Boc)-OH (5.32 g, 15.4 mmol) in 18.8 mL of DMSO (anhydrous), EDC HCl (2.76 g, 14.4 mmol), HOBt.H$_2$O (2.20 g, 14.4 mmol), and 10.0 mL of collidine (76.8 mmol) were added. The reaction mixture was stirred for 60 min at RT.

The reaction mixture was diluted with 800 mL of DCM and washed with 100 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried over Na$_2$SO$_4$, filtered and evaporated to give crude product 2f as colorless oil.

Product was dissolved in DCM and precipitated with cooled (−18° C.) diethylether. This step was repeated twice and the precipitate was dried in vacuo.

Yield 1.72 g (82%) colourless glassy product 2f which was used in the next step without further purification.

MS: m/z 1505.3=[M+8H]$^{8+}$ (MW calculated=1505.4).

Backbone reagent 2g was obtained by stirring a solution of compound 2f (MW ca 12035 g/mol, 4.72 g, 0.39 mmol) in 20 mL of methanol and 40 mL of 4 N HCl in dioxane at RT for 30 min. Volatiles were removed in vacuo.

Yield 3.91 g (100%), glassy product backbone reagent 2g.

MS: m/z 977.2=[M+9H]$^{9+}$ (MW calculated=977.4).

Synthesis of Backbone Reagent 2h

[PEG500-LysLys₂Lys₄(NH₂)₈]₄ =
2h

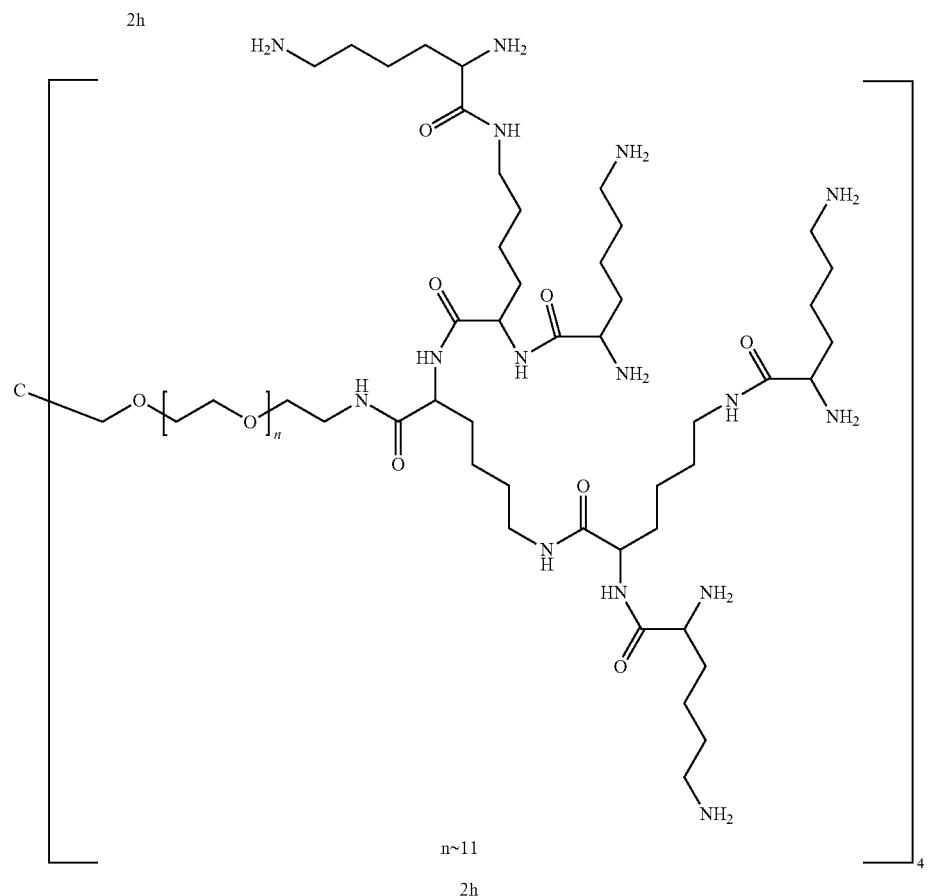

n~11

2h

Backbone reagent 2h was synthesized as described for 2g except for the use of 4-arm PEG2000 instead of 4-arm PEG5000.

MS: m/z 719.4=[M+9H]$^{8+}$ (MW calculated=719.5).

Example 3

Synthesis of Crosslinker Reagents (3d), (3e), and (3f)

Crosslinker reagent 3d was prepared from adipic acid mono benzyl ester (English, Arthur R. et al., *Journal of Medicinal Chemistry*, 1990, 33(1), 344-347) and PEG2000 according to the following scheme:

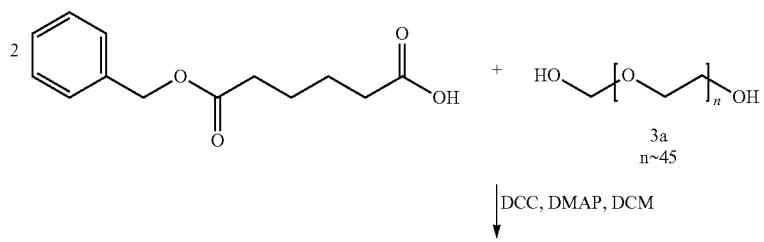

DCC, DMAP, DCM

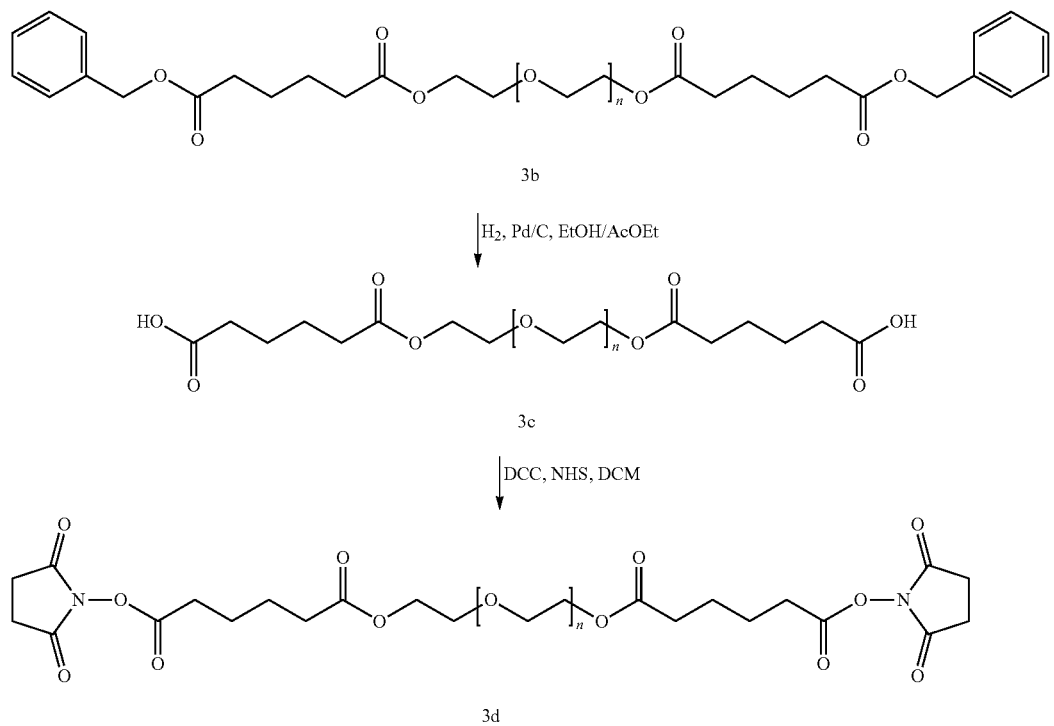

3b

↓ H₂, Pd/C, EtOH/AcOEt

3c

↓ DCC, NHS, DCM

3d

A solution of PEG2000 (3a) (11.0 g, 5.5 mmol) and benzyl adipate half ester (1.8 g, 20.6 mmol) in dichloromethane (90.0 mL) was cooled to 0° C. Dicyclohexylcarbodiimide (4.47 g, 21.7 mmol) was added followed by a catalytic amount of DMAP (5 mg) and the solution was stirred and allowed to reach RT overnight (12 h). The flask was stored at +4° C. for 5 h. The solid was filtered and the solvent completely removed by destillation in vacuo. The residue was dissolved in 1000 mL 1/1 (v/v) diethyl ether/ethyl acetate and stored at RT for 2 hours while a small amount of a flaky solid was formed. The solid was removed by filtration through a pad of Celite®. The solution was stored in a tightly closed flask at −30° C. in the freezer for 12 h until crystallisation was complete. The crystalline product was filtered through a glass frit and washed with cooled diethyl ether (−30° C.). The filter cake was dried in vacuo.

Yield: 11.6 g (86%) 3b as a colorless solid. The product was used without further purification in the next step.

MS: m/z 813.1=[M+3H]$^{3+}$ (MW calculated=813.3)

In a 500 mL glass autoclave PEG2000-bis-adipic acid-bis-benzyl ester 3b (13.3 g, 5.5 mmol) was dissolved in ethyl acetate (180 mL) and 10% Palladium on charcoal (0.4 g) was added. The solution was hydrogenated at 6 bar, 40° C. until consumption of hydrogen had ceased (5-12 h). Catalyst was removed by filtration through a pad of Celite® and the solvent was evaporated in vacuo.

Yield: 12.3 g (quantitative) 3c as yellowish oil. The product was used without further purification in the next step.

MS: m/z 753.1=[M+3H]$^{3+}$ (MW calculated=753.2)

A solution of PEG2000-bis-adipic acid half ester 3c (9.43 g, 4.18 mmol), N-hydroxysuccinimide (1.92 g, 16.7 mmol) and DCC (3.44 g, 16.7 mmol) in 75 mL of DCM (anhydrous) was stirred over night at RT. The reaction mixture was cooled to 0° C. and precipitate was filtered off. DCM was evaporated and the residue was recrystallized from THF.

Yield: 8.73 g (85%) crosslinker reagent 3d as colorless solid.

MS: m/z 817.8=[M+3H]$^{3+}$ (MW calculated=817.9).

Synthesis of 3e

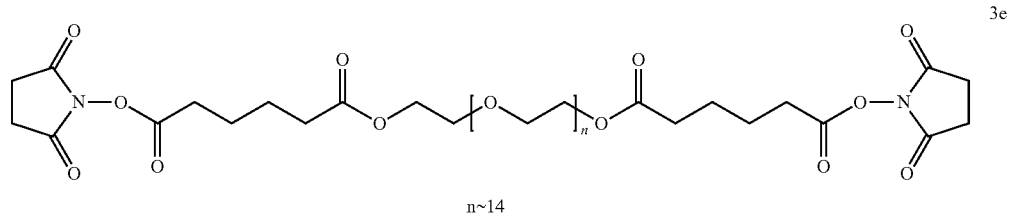

n~14

3e was synthesized as described for 3d except for the use of PEG600 instead of PEG2000.

MS: m/z 997.5=[M+H]$^{+}$ (MW calculated=997.8)

Synthesis of 3f

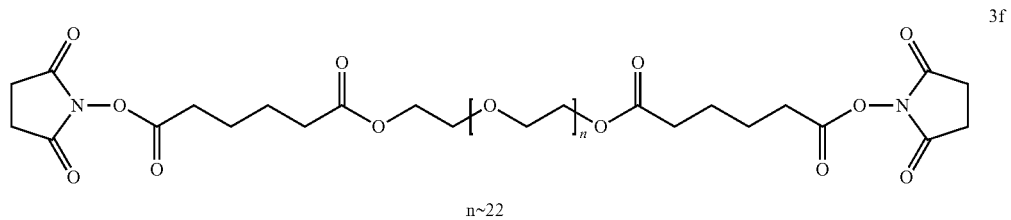

n~22

3f was synthesized as described for 3d except for the use of PEG1000 instead of PEG2000.
MS: m/z 697.4=[M+2H]$^{2+}$ (MW calculated=697.3)

Synthesis of 3g

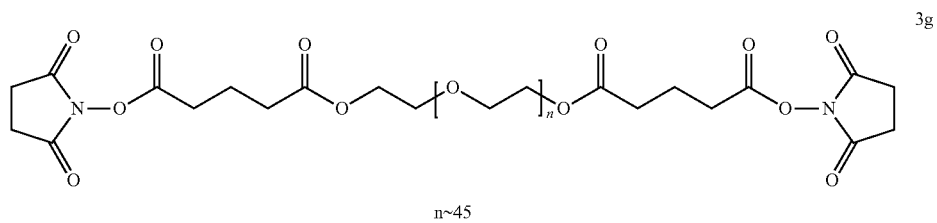

n~45

3g was synthesized as described for 3d except for the use of glutaric acid instead of adipic acid.
MS: m/z 764.4=[M+3H]$^{3+}$ (MW calculated=764.5).

Example 4

Preparation of Hydrogel Beads (4a), (4b), (4c) and (4d) Containing Free Amino Groups A solution of 720 mg 2g and 1180 mg 3d in 7.3 mL DMSO was added to a solution of 300 mg Arlacel P135 (Croda International Plc) in 60 mL heptane. The mixture was stirred at 1200 rpm with a custom metal stirrer for 10 min at RT to form a suspension. 2.6 mL N,N,N',N'-tetramethylethylenediamine (TMEDA) was added to effect polymerization. After 2 h, the stirrer speed was reduced to 500 rpm and the mixture was stirred for additional 16 h. 4 mL of acetic acid were added and then after 10 min 50 mL of water were added. After 5 min, the stirrer was stopped and the aqueous phase was drained.

For bead size fractionation, the water-hydrogel suspension was wet-sieved on 75, 50, 40, 32 and 20 μm steel sieves. Bead fractions that were retained on the 32, 40, and 50 μm sieves were pooled and washed 3 times with water, 10 times with ethanol and dried for 16 h at 0.1 mbar to give 4a as a white powder.

4b was prepared as described for 4a except for the use of 900 mg 2g, 886 mg 3f, 6.7 ml DMSO, 3.2 ml TMEDA, 5.0 ml acetic acid and a stirring speed of 1500 rpm.

4c was prepared as described for 4a except for the use of 1200 mg 2h, 1300 mg 3e, 9.9 ml DMSO, 6.1 ml TMEDA, 9.4 ml acetic acid and a stirring speed of 1000 rpm.

4d was prepared as described for 4a except for the use of 1180 mg of 3g instead of 3d.

Quantification of Free Amino Groups in Hydrogel Beads.
Free amino groups were quantified according to a method used for amino group quantification of solid phase synthesis resins (M. (Gude, J. Ryf, P. D. White, *Lett. Pept. Sci.*, 2002, 9, 203-206).

|    | amine content [mmol/g] |
|----|------------------------|
| 4a | 0.82-0.93              |
| 4b | 0.99-1.18              |
| 4d | 0.84-0.93              |

Example 5

Synthesis of Ado-Modified Hydrogels (5a), (5b), and (5c) and Lys-Modified Hydrogels (5d) and (5e)

Synthesis of Ado-Modified Hydrogel (5a, 5b, 5c):

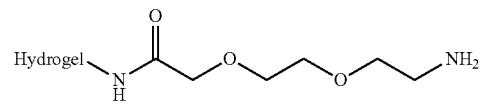

Hydrogel 4a, 4b, and 4c, respectively, in a syringe equipped with a polypropylene frit was washed with 1% diisopropylethylamine solution in DMF and ten times with DMF.

Fmoc-Ado-OH coupling was then performed by agitating 4a, 4b, and 4c, respectively, with 3.5 eq of Fmoc Ado-OH, 3.5 eq of PyBOP and 8.75 eq of DIPEA in DMF (using 0.2 mmol/mL Fmoc-Ado-OH concentration). After 45 min, hydrogel was washed with DMF (10 times), then with DCM (10 times).

Fmoc-deprotection was achieved by agitating the hydrogel two times with a 96/2/2 DMF/piperidine/DBU (v/v) solution for 5 min each. 5a, 5b, and 5c, respectively, was then washed with DMF (10 times) and ethanol (10 times) and finally dried in vacuo.

Synthesis of Lys-Modified Hydrogels (5d) and (5e):

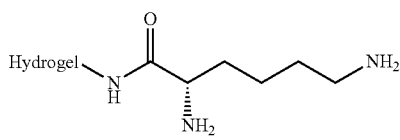

Hydrogel 4a in a syringe equipped with a polypropylene frit was washed with 1% diisopropylethylamine solution in DMF and ten times with DMF.

Fmoc-Lys(Fmoc)-OH coupling was then performed by agitating 4a and 4d, respectively, with 3.5 eq of Fmoc-Lys (Fmoc)-OH, 3.5 eq of PyBOP and 8.75 eq of DIPEA in DMF (using 0.2 mmol/mL Fmoc-Lys(Fmoc)-OH concentration). After 45 min, hydrogel was washed with DMF (10 times), then with DCM (10 times).

Fmoc-deprotection was achieved by agitating the hydrogel two times with a 96/2/2 DMF/piperidine/DBU (v/v) solution for 5 min each. 5d and 5e, respectively, was then washed with DMF (10 times) and ethanol (10 times) and finally dried in vacuo.

Example 6

Synthesis of Paliperidone-Linker-Hydrogel (6a), (6b), (6c), (6d), (6e), (6f), (6g), (6h), (6i) and (6j)

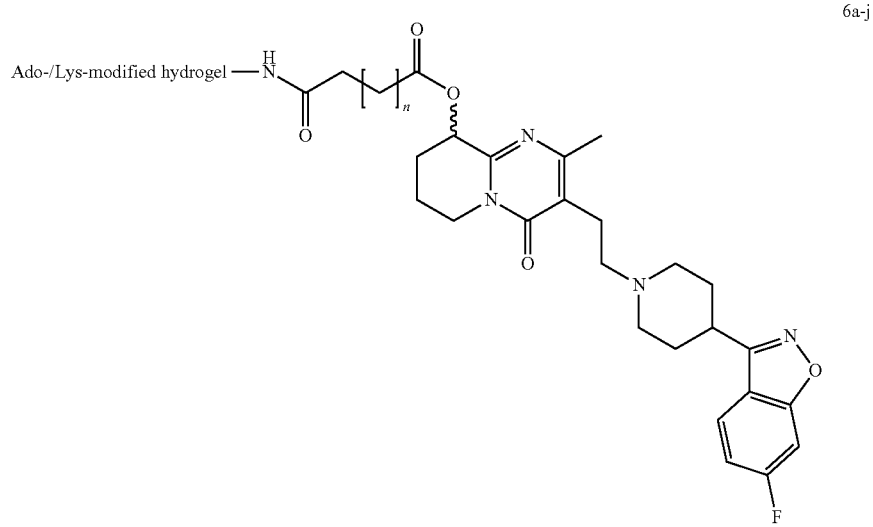

6a-j

General Protocol for Paliperidone-Linker Coupling:

5c (1 eq amine content) was weighed into a syringe equipped with a polypropylene frit and agitated with 3 eq of paliperidone-ester 1a, 3 eq of PyBOP, and 7.5 eq of DIPEA in dry DMF (using 0.2 mmol/mL concentration of paliperidone-ester 1a) for 2 h. Paliperidone-linker-hydrogel 6a was washed with DMF (8 times), then with a 96/2/2 v/v DMF/piperidine/ DBU solution (10 times), then further washed with DMF (10 times) and finally with a ACN/water 1/1+0.1% TFA solution (10 times).

Paliperidone loading was determined by total hydrolysis of paliperidone-linker-hydrogel samples at pH 12 for 4 h at 37° C. and quantification of released paliperidone by UPLC and detection at 280 nm using a paliperidone calibration curve.

6c, 6d, 6e, 6f, 6g, 6h, 6i and 6j respectively, were synthesized as described above except for the use of hydrogel 5c, 5a, 5b, 5a, 5d 5d, 5d, 5e, and 5e, respectively, and paliperidone ester 1b, 1a, 1a, 1c, 1a, 1c, 1d, 1d and 1e, respectively.

Paliperidone loading of different paliperidone-linker-hydrogels is summarized in table 1:

TABLE 1

| Compound | Hydrogel | Paliperidone-linker | Paliperidone loading (% w/w) |
|---|---|---|---|
| 6a | 5c | 1a | 27% |
| 6b | 5c | 1b | 33% |
| 6c | 5a | 1a | 24% |
| 6d | 5b | 1a | 18% |
| 6e | 5a | 1c | 23% |
| 6f | 5d | 1a | 34% |
| 6g | 5d | 1c | 34% |
| 6h | 5d | 1d | 36% |
| 6i | 5e | 1d | 37% |
| 6j | 5e | 1e | 28% |

Example 7

In Vitro Release Kinetics

In Vitro Release Studies at pH 7.4:

Paliperidone-linker-hydrogel samples (in duplicate) containing approximately 0.85 mg paliperidone were washed three times with pH 7.4 phosphate buffer (60 mM, 3 mM EDTA, 0.01% Tween-20) and filled-up to 1.5 mL using the same buffer. Samples were incubated at 37° C. and aliquots of supernatant were analyzed at various time points by UPLC and detection at 280 nm. Peaks corresponding to released paliperidone were integrated and the amount of released paliperidone calculated by comparison with a paliperidone calibration curve. The amount of released paliperidone was plotted versus time and half-life of release was determined using curve-fitting software assuming first-order release kinetics.

In vitro release kinetics of 6a is shown in FIG. 1.

Half-life times of other hydrogel linkers are disclosed in table 2:

TABLE 2

| Ref. | $t_{1/2}$ (d) |
|---|---|
| 6a | 17 |
| 6b | 53 |
| 6c | 19 |
| 6d | 15 |
| 6e | 28 |
| 6f | 28 |
| 6g | 44 |
| 6h | 17 |
| 6i | 15 |

Example 8

Paliperidone Pharmacokinetics Study in Rat

The pharmacokinetics of 6c was determined by measuring the plasma paliperidone concentration after subcutaneous application of a single dose into rats.

One group consisting of 5 male Wistar rats (200-250 g) was used to study the plasma paliperidone levels over a period of 28 days. Each of the animals received a single subcutaneous injection of 500 µL 6c suspension in acetate buffer pH 5, containing 7 mg paliperidone (14 mg paliperidone/ml). Per animal and time point 200 µL of blood was withdrawn sublingually to obtain 100 µL Li-Heparin plasma. Samples were collected before application and after 4 h, 2, 4, 7, 11, 14, 18, 21, 25 and 28 days post injection. Plasma samples were frozen within 15 min after blood withdrawal and stored at −80° C. until assayed.

Figure 2A:
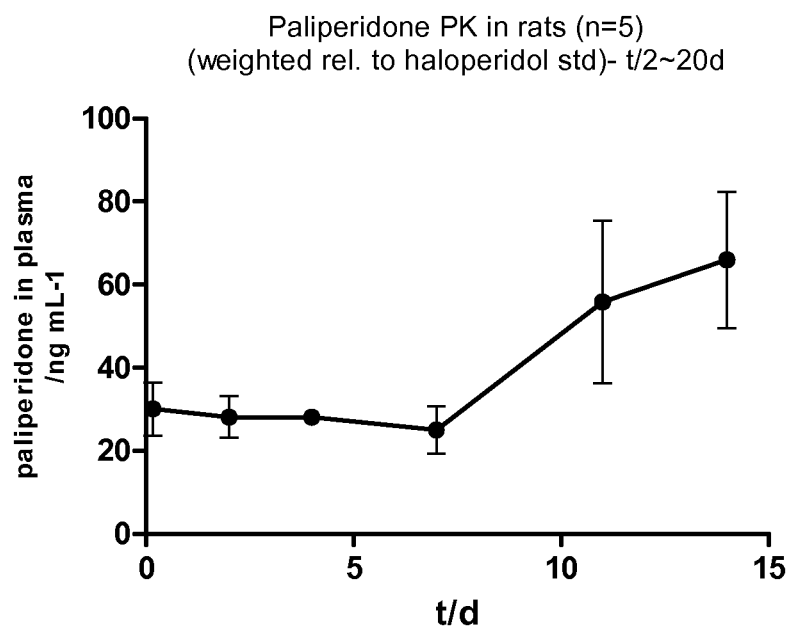
FIG. 2a shows the pharmacokinetics of compound 6c in rat for days 1 to 14.
Figure 2B:
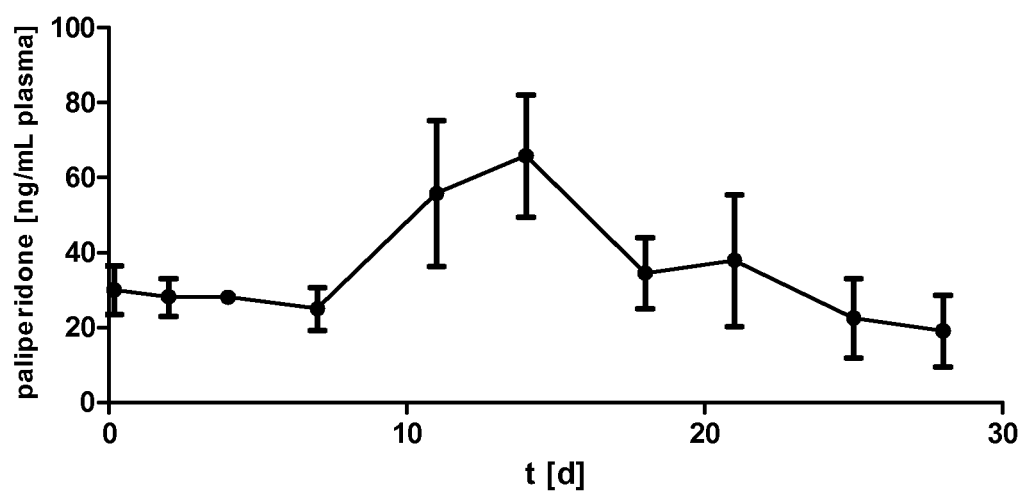
FIG. 2b shows the pharmacokinetics of compound 6c in rat for days 1 to 28.

Plasma samples were assayed for paliperidone content as described in Materials and Methods. The results are shown in FIG. 2. No burst of paliperidone and a sustained release of paliperidone over 28 days was observed.

Figure 3A:
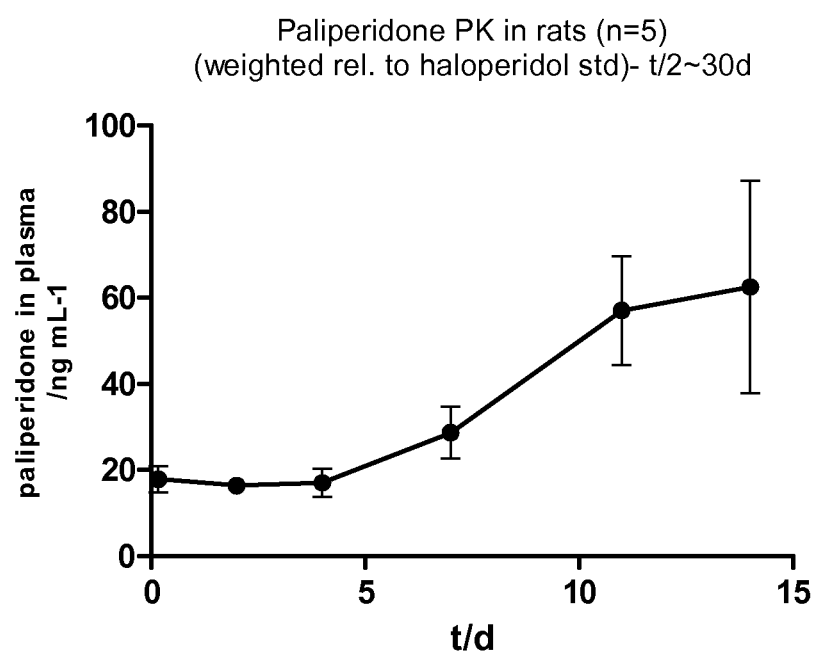
FIG. 3a shows the pharmacokinetics of compound 6e in rat for days 1 to 14.
Figure 3B:
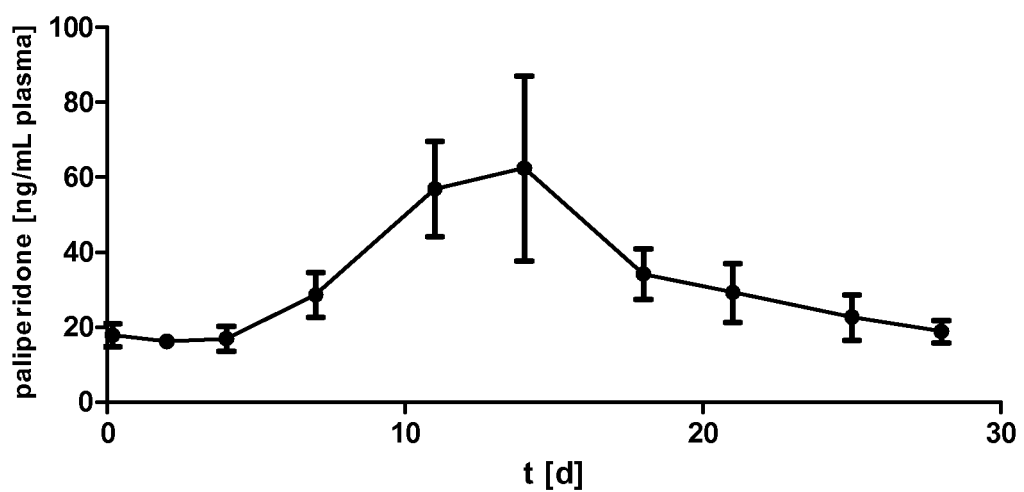
FIG. 3b shows the pharmacokinetics of compound 6e in rat for days 1 to 28.

The pharmacokinetics of 6e were measured as described for 6c. The results are shown in FIG. 3. No burst of paliperidone and a sustained release of paliperidone over 28 days was observed.

Example 9

Paliperidone Pharmacokinetics Study in Rabbit

The pharmacokinetics of 6i was determined by measuring the plasma paliperidone concentration after subcutaneous application of a single dose into rabbits.

One group consisting of 5 male rabbits (New Zealand white, 2.5-3.0 kg) was used to study the plasma paliperidone levels over a period of 28 days. Each of the animals received a single subcutaneous injection of 6i suspension (18 mg paliperidone/kg, 54 mg paliperidone/ml) in succinate/Tris buffer pH 5. Per animal and time point 200 µL of blood was withdrawn to obtain 100 µL Li-Heparin plasma. Samples were collected before application and after 4 h, 1, 2, 4, 7, 9, 11, 14, 16, 18, 21, 23, 25 and 28 days post injection. Plasma samples were frozen within 15 min after blood withdrawal and stored at −80° C. until assayed.

Figure 4:
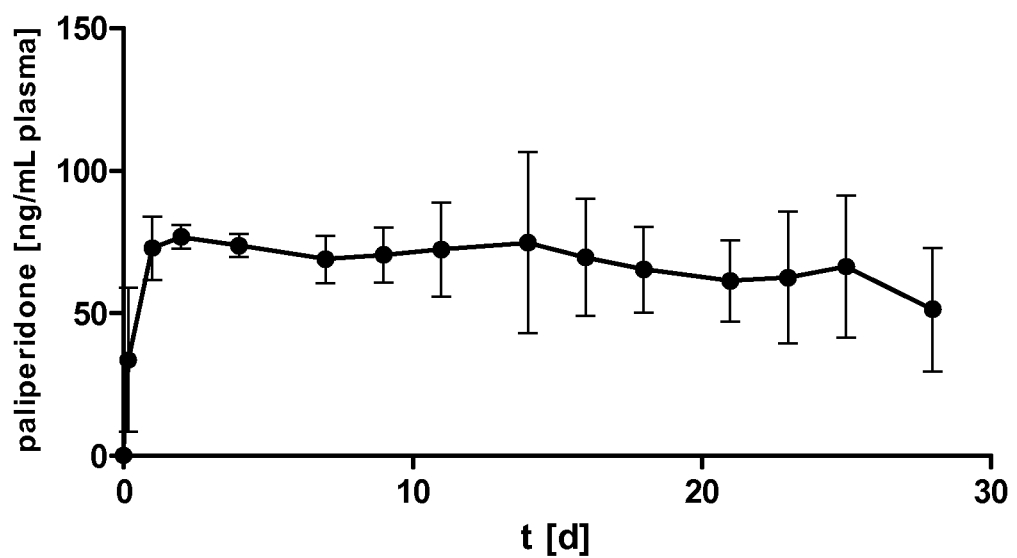
FIG. 4 shows the pharmacokinetics of compound 6i in rat.

Plasma samples were assayed for paliperidone content as described in Materials and Methods. The results are shown in FIG. 4. No burst of paliperidone and a sustained release profile of paliperidone over 28 days was observed.

Example 10

Paliperidone Release Kinetics and Hydrogel Degradation Kinetics

Figure 5:
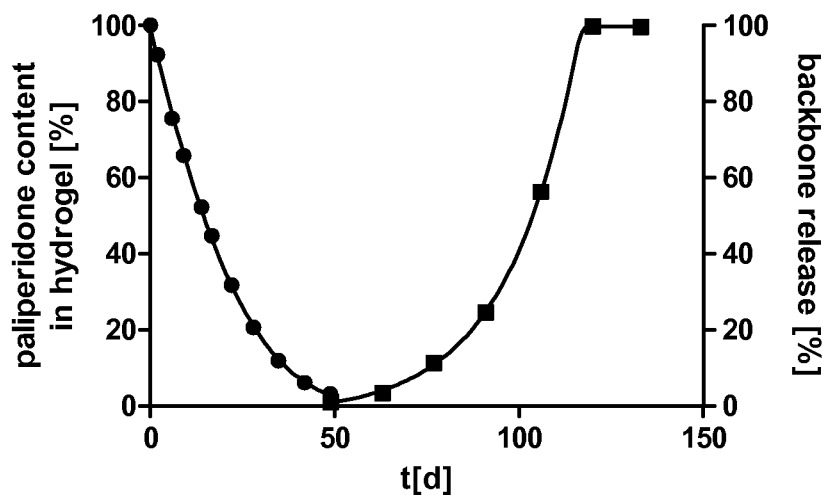
FIG. 5 shows combined data of paliperidone release and hydrogel degradation kinetics of compound 6l in vitro at pH 7.4 and 37° C.

Paliperidone linker hydrogel 6i was incubated in pH 7.4 buffer at 37° C. and paliperidone release was monitored as described in Example 7. Hydrogel degradation was monitored by release of backbone containing moieties by SEC as described in "Materials and Methods". Result: During lag phase of hydrogel degradation (50 days) approx. 95% of paliperidone is released due to matched paliperidone prodrug linker kinetics and hydrogel degradation kinetics. Hydrogel degradation was complete after 125 days, FIG. 5.

Example 11

Preparation of a of Dense Paliperidone-Linker Hydrogel Suspension and 30 G Needle Test The following formulation buffer was used: 10 mM succinic acid, 85 g trehalose dihydrate/L, 0.3% (weight) Pluronic F68 and 0.01%-Tween 20 (weight) were dissolved in water and pH 5.0 was adjusted with 1 M Tris base. Hydrogel suspension 6f was washed five times with formulation buffer. Hydrogel was left settling at 4° C. for 1 day and the supernatant was removed in order to obtain a dense suspension. The weight of the dense suspension was determined, the suspension was lyophilized and the weight loss was determined.

The lyophilization cake was reconstituted by addition of an amount of water corresponding to the weight loss during lyophilization. The suspension was homogenized by gentle shaking. Suspension was drawn into a 1 mL Luer-lock syringes via a 20 G needle. The needle was exchanged to a 30 G needle. The suspension was ejected from the syringe manually. The suspension passed the needle without blocking.

Example 12

Stability Test

A dense suspension of 6f was prepared as described in Example 11. Aliquots were transferred in 1.5 mL glass vials, samples were frozen in liquid nitrogen and lyophilized over night at RT and 0.05 mbar. Lyophilized samples were stored at 37° C.

At given time aliquots were reconstituted by addition of water/acetonitrile (1/1 v/v). Samples were vortexed and centrifuged. The supernatant was assayed for liberated paliperidone as described in Example 7.

Result: After 120 days 0.75% paliperidone was liberated.

Example 13

Alternative Synthesis of 6i

Synthesis of Compound 17a

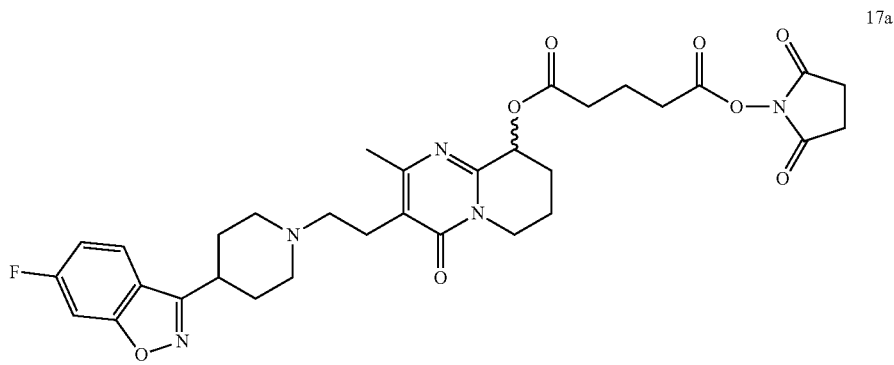 [SMILES: Cc1nc2n(c(=O)c1CCN1CCC(c3noc4cc(F)ccc34)CC1)CCCC2OC(=O)CCCC(=O)ON1C(=O)CCC1=O]

6d (1.50 g, 2.77 mmol) was dissolved in 40 mL DCM (dry, mol. sieve). DCC (1.72 g, 8.32 mmol), N hydroxy succinimide (1.60 g, 13.87 mmol) and catalytic amount of DMAP was added and mixture was stirred for 3 h at RT. Precipitate was filtered off and the solvent was removed under reduced pressure. Residue was dissolved in a mixture of water and acetonitrile and 17a was purified by RP-HPLC. After lyophilization 17a was obtained as a white solid.

Yield: 1.25 g (TFA salt, 1.66 mmol, 60%).
MS: m/z 638.25=[M+H]$^+$ (MW calculated=637.67)

Synthesis of Compound 17b

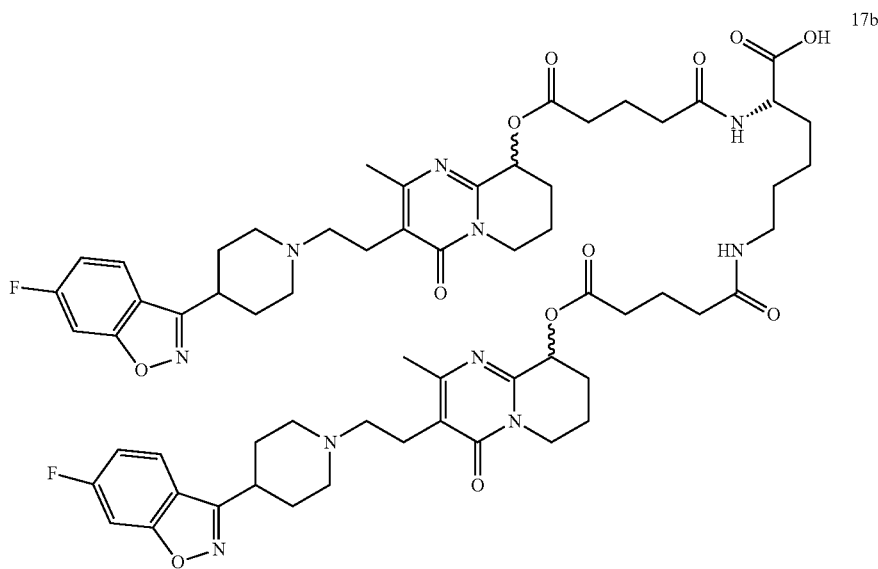

A solution of L-lysine (19 mg, 0.13 mmol) in 2.5 mL 0.5 M sodium borate buffer pH 8.5 was given to a solution of 17b (TFA salt, 300 mg, 0.40 mmol) in 5 mL DMSO. Mixture was stirred for 60 min at RT. Solution was acidified with acetic acid and diluted with water and acetonitrile. 17a was purified by RP-HPLC. After lyophilization 17a was obtained as a white solid.

Yield: 125 mg (HCl salt, 0.10 mmol, 74%).
MS: m/z 1191.55=[M+H]$^+$ (MW calculated=1191.35)

Synthesis of Compound 17c

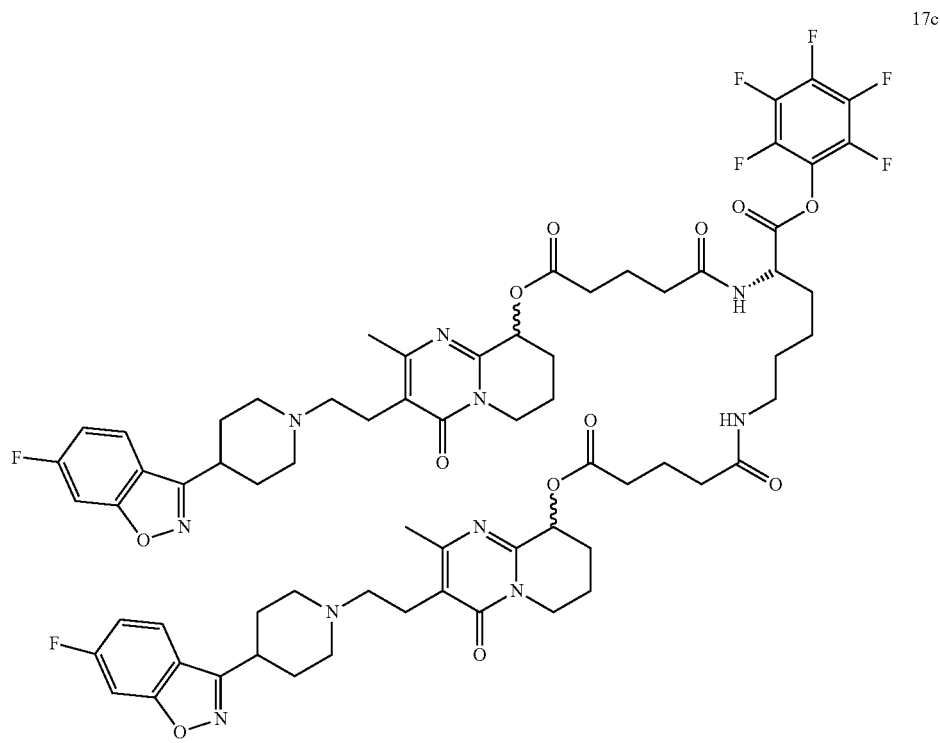

17b (bis HCl salt, 196 mg, 0.155 mmol) was dissolved in 8 mL DMSO (dry, mol. sieve). Bis(pentafluorophenyl) carbonate (309 mg, (0.784 mmol) and sym-collidine (353 µl, 2.65 mmol) were added and mixture was stirred for 6 h at RT. Mixture was diluted with water and acetonitrile and acidified with acetic acid in order to obtain a pH of 4. 17c was purified by RP-HPLC. After lyophilization 17c obtained as a white solid.

Yield: 48 mg of a 1/1 mixture (215 nm) of 17c and 17b.
MS: m/z 1357.52=[M+H]$^+$ (MW calculated=1357.40)

Synthesis of 6i 6i was synthesized as described in Example 6 except that hydrogel 5e and paliperidone active ester 17c were used and PyBOP was omitted.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

ABBREVIATIONS

ACN acetonitrile
AcOEt ethyl acetate
AcOH acetic acid
Ado 8-amino-3,6-dioxa-octanoic acid
Boc t-butyloxycarbonyl
DBU 1,3-diazabicyclo[5.4.0]undecene
DCC dicyclohexylcarbodiimide
DCM dichloromethane
DIPEA diisopropylethylamine
DMAP dimethylamino-pyridine
DMF N,N-dimethylformamide
DMSO dimethylsulfoxide
EDC 1-Ethyl-3-(3-dimethylaminopropyl)carbodiimide
EDTA ethylenediaminetetraacetic acid
ESI electrospray ionization
EtOH ethanol
eq stoichiometric equivalent
Fmoc 9-fluorenylmethoxycarbonyl
HFIP hexafluoroisopropanol
HOBt N-hydroxybenzotriazole
LCMS mass spectrometry-coupled liquid chromatography
MeOH methanol
MS mass spectrum/mass spectrometry
MW molecular weight
NHS N-hydroxy succinimide
PEG poly(ethylene glycol)
PyBOP benzotriazole-1-yl-oxy-tris-pyrrolidino-phosphonium hexafluorophosphate
RP-HPLC reversed-phase high performance liquid chromatography
RT room temperature
s.c. sub-cutaneous
TES triethylsilane
TFA trifluoroacetic acid
THF tetrahydrofuran
TMEDA N,N,N',N', tetramethyl ethylene diamine
UPLC ultra performance liquid chromatography
UV ultraviolet

We claim:
1. A pharmaceutical composition for subcutaneous injection comprising:
a paliperidone compound;
wherein the composition, after subcutaneous injection, releases the paliperidone with an immediate onset of action and continuously for at least 3 weeks;

wherein the composition has a pharmacokinetic profile in vivo with substantially no burst release of the paliperidone; and
wherein the paliperidone compound is covalently linked in a depot.

2. The pharmaceutical composition of claim 1;
wherein the paliperidone is released in such way that therapeutic plasma levels are reached within 24 hours of administration.

3. The pharmaceutical composition of claim 1;
wherein the composition has a pharmacokinetic profile in vivo with no burst release of the paliperidone.

4. The pharmaceutical composition of claim 1;
wherein a concentration of the paliperidone compound is at least 10 mg/ml based on quantitative release of free paliperidone from the compound.

5. The pharmaceutical composition of claim 1;
wherein the composition exhibits a peak to trough ratio of released paliperidone of less than 10.

6. The pharmaceutical composition of claim 1;
wherein the paliperidone compound is a prodrug.

7. The pharmaceutical composition of claim 1;
wherein the paliperidone compound is fully contained in a depot.

8. The pharmaceutical composition of claim 1;
wherein the paliperidone compound is formulated as particles.

9. The pharmaceutical composition of claim 8;
wherein the paliperidone compound is formulated in polyethylene glycol-based hydrogel particles.

10. A pharmaceutical composition according to claim 1;
wherein the paliperidone compound is a prodrug, and is formulated in a hydrogel; and
wherein the paliperidone hydrogel prodrug is sufficiently dosed in the composition to provide a therapeutically effective amount of paliperidone for at least one week in one application.

11. A method of treating a psychotic disease or disorder in a subject, comprising:
utilizing the pharmaceutical composition of claim 1.

12. The composition of claim 1;
wherein the composition does not change physical state before, during, and immediately after administration.

13. A method of treating a psychotic disease or disorder selected from the group consisting of delusional psychosis, psychotic depression, obsessive-compulsion disorder, schizophrenia, bipolar disorder, Asperger's syndrome, Tourette's syndrome, autistic spectrum disorders, and any combination thereof, in a subject in need of such a treatment, comprising:
administering a therapeutically effective amount of a composition of claim 1.

14. A kit of parts comprising:
a pharmaceutical composition of claim 1; and
a container for administration of the composition.

* * * * *